United States Patent
Park et al.

(10) Patent No.: US 8,626,278 B2
(45) Date of Patent: Jan. 7, 2014

(54) METHOD AND SYSTEM FOR DISCRIMINATING AND MONITORING ATRIAL ARRHYTHMIA BASED ON CARDIOGENIC IMPEDANCE

(76) Inventors: Euljoon Park, Valencia, CA (US); Steve Koh, South Pasadena, CA (US); Gene A. Bornzin, Simi Valley, CA (US)

( * ) Notice: Subject to any disclaimer, the term of this patent is extended or adjusted under 35 U.S.C. 154(b) by 511 days.

(21) Appl. No.: 12/901,296

(22) Filed: Oct. 8, 2010

(65) Prior Publication Data

US 2012/0089032 A1 Apr. 12, 2012

(51) Int. Cl.
*A61B 5/0464* (2006.01)
*A61B 5/053* (2006.01)

(52) U.S. Cl.
USPC .............. 600/515; 600/513; 600/518; 607/24

(58) Field of Classification Search
USPC ............. 607/9, 14, 17, 24; 600/513, 515, 518
See application file for complete search history.

(56) References Cited

U.S. PATENT DOCUMENTS

| | | | |
|---|---|---|---|
| 5,078,133 A | 1/1992 | Heinz et al. | |
| 5,170,785 A | 12/1992 | Heinz et al. | |
| 5,183,040 A * | 2/1993 | Nappholz et al. | 607/4 |
| 6,658,292 B2 * | 12/2003 | Kroll et al. | 607/19 |
| 6,986,741 B2 | 1/2006 | Poliac et al. | |
| 7,149,573 B2 | 12/2006 | Wang | |
| 7,254,440 B1 * | 8/2007 | Kroll | 600/517 |
| 7,305,266 B1 * | 12/2007 | Kroll | 607/28 |
| 7,894,900 B2 * | 2/2011 | Kink et al. | 607/17 |
| 7,925,348 B1 | 4/2011 | Bornzin et al. | |
| 8,239,011 B2 * | 8/2012 | Li | 600/518 |
| 2002/0002389 A1 * | 1/2002 | Bradley et al. | 607/8 |
| 2005/0070986 A1 | 3/2005 | Tockman et al. | |
| 2009/0099614 A1 | 4/2009 | Holmstrom et al. | |
| 2011/0004264 A1 | 1/2011 | Siejko et al. | |

FOREIGN PATENT DOCUMENTS

WO 2007100276 A1 9/2007

OTHER PUBLICATIONS

Patterson, R.P., "Fundamentals of Impedance Cardiography," IEEE Engineering in Medicine and Biology Magazine. Mar. 1989:35-38.

* cited by examiner

*Primary Examiner* — Carl H Layno
*Assistant Examiner* — Eugene Wu

(57) ABSTRACT

A medical device is provided that comprises a lead assembly. The lead assembly includes at least one intra-cardiac (IC) electrode, an extra-cardiac (EC) electrode and a subcutaneous remote-cardiac (RC) electrode. The IC electrode is configured to be located within the heart. The EC electrode is configured to be positioned proximate to at least one of a superior vena cava (SVC) and a left ventricle (LV) of a heart. The RC electrode is configured to be located remote from the heart. An extra-cardiac impedance (ECI) module is configured to measure extra-cardiac impedance along an ECI vector between the EC and RC electrodes to obtain ECI measurements. An arrhythmia monitoring module is configured to declare a potential atrial arrhythmia to be an atrial arrhythmia based on the hemodynamic performance determined from the ECI measurements. The hemodynamic performance assessment module is further enabled to compare a current ECI pattern with a prior baseline ECI waveform.

21 Claims, 12 Drawing Sheets

METHOD AND SYSTEM FOR DISCRIMINATING AND MONITORING ATRIAL ARRHYTHMIA BASED ON CARDIOGENIC IMPEDANCE

FIELD OF THE INVENTION

Embodiments of the present invention generally relate to methods and systems to discriminate and monitor arrhythmias based on cardiogenic impedance.

BACKGROUND OF THE INVENTION

Atrial fibrillation has been characterized by a rapid irregular heartbeat and can be intermittent or permanent in nature. Atrial fibrillation (AF) is caused by a dysfunction of the heart tissue or nodes, by a dysfunction of the autonomic nervous system or by a combination thereof. Individual heart cells are capable of beating outside of the control of the autonomic system. Sometimes, agglomerations of very active cells form and create a focus which results in ectopic beats, namely beats that originate at a location within the heart other than the sino-atrial (SA) node. The junction between the left atrium and the pulmonary vein may be a common location where ectopic beats originate from cell agglomerations.

If left untreated, ectopic beats may become very frequent and run together with one another, thereby creating atrial fibrillation. Atrial fibrillation involves a chaotic movement of electrical impulses across the atria. Atrial fibrillation may lead to a loss of synchrony between the atria and the ventricles. Once an episode of atrial fibrillation has begun, the atria may quiver or fibrillate at a rate as high as 300-600 times per minute. Such high fibrillation causes a very inefficient filling and emptying process of the atria. The chaotic quivering behavior of the atria may then be transferred to the ventricles and cause the ventricles to lose a regular rhythmic behavior and begin to contract fast and/or in a totally irregular manner. This type of chaotic transfer to the ventricles often gives rise to the fast and irregular pulse rate felt during an AF episode (e.g. between 90 and 160 per minute).

Atrial flutter is another atrial arrhythmia that is characterized by rapid atrial behavior. Atrial flutter may sometimes go unnoticed, yet its onset is often marked by characteristic sensations of regular palpitations. These sensations may last until the episode resolves or until the heart rate becomes under control. Atrial flutter is usually well tolerated initially, as the high heart rate is similar to the heart rate that a person experiences during normal exercise. However, some patients with underlying heart disease or poor exercise tolerance may rapidly develop adverse symptoms which can include shortness of breath, chest pains, light headedness or dizziness, nausea and, in some patients, nervousness and feelings of impending doom. Prolonged fast flutter may lead to decompensation with loss of normal function and potential heart failure. Prolonged fast flutter may manifest as breathlessness, nocturnal breathlessness, swelling of the lungs and swelling of the abdomen.

IMDs detect various arrhythmias such as atrial fibrillation (AF), atrial flutter (A-Flutter), and atrial tachycardia (AT) (hereafter collectively atrial arrhythmias). Arrhythmias are detected based on one or more of ventricular rate, rate stability, and the morphology of the cardiac signal. However, conventional algorithms for detecting arrhythmias experience certain limitations. For example, conventional AF detection algorithms that are based on rate stability may become confounded when an atrial tachyarrhythmia drives a ventricle at a high, but very stable rate. When a patient experiences atrial tachyarrhythmia having a stable rate, the AF detection algorithm may classify the events merely as high rate normal sinus events. Thus, the AF detection algorithm may not declare the events to be pathologic (non-physiologic) and may not deliver a therapy. Further, conventional algorithms may not correctly classify atrial fibrillation that exhibits rate dependent changes in the QRS complex. When a patient experiences atrial tachyarrhythmia having rate dependent changes in the QRS complex, the morphology detection algorithm may classify the events merely as physiologic events and thus, may not declare the events to be pathologic.

At least certain limitations of conventional detection algorithms extend, in part, from the fact that the algorithms analyze IEGM signals from various combinations of electrodes within and surrounding the heart. IEGM signals are a direct indicator of the electrical activity within the tissue of the heart. While heart tissue electrical activity is a good surrogate of heart electrical behavior, the electrical activity is not directly correlated to the resultant actual "mechanical" output of the heart. The mechanical output of the heart constitutes the actual cardiac output (CO) of the heart. Cardiac output represents a volume of blood that is ejected from the heart over a period of time. For example, the cardiac output may be quantified in terms of the stroke volume (SV) (ml/heart beat) times the heart rate (beats/minute). While IEGM signals are a good approximation of cardiac output, IEGM signals are not a direct surrogate of hemodynamic performance.

Heretofore, various intra-cardiac indicators (ICI) have been proposed for monitoring cardiac activity, such as heart sounds, blood pressure, and the like. It has also been proposed to monitor certain types of intra-cardiac impedance (within the heart) to derive hemodynamic performance. Intra-cardiac impedance represents impedance that is measured between electrodes that are located within the heart (intra-cardiac electrodes). For example, the intra-cardiac electrodes may be located within the right atrium and the right ventricle with the intra-cardiac impedance measured therebetween. The intra-cardiac electrodes define an intra-cardiac impedance vector that extends through one or both of the atrium and ventricle. The entire intra-cardiac impedance vector or at least a substantial majority of the intra-cardiac impedance vector lies within, and extends through, the blood pool in the chambers of the heart.

Intra-cardiac impedance exhibits a high value when the associated heart chamber(s) are in a systole state. The intra-cardiac impedance exhibits a low value when the associated heart chamber(s) are in a diastole state. As the corresponding heart chambers transition between systole and diastole, the impedance waveform moves between peaks and valleys. The intra-cardiac impedance waveform has not proven to be a good surrogate of stroke volume or hemodynamic performance. One limitation of the intra-cardiac impedance waveform arose from the fact that the intra-cardiac impedance vector extends through multiple chambers of the heart. Thus, each measurement of intra-cardiac impedance includes components from individual chambers of the heart, not the overall cooperative effect of all of the heart chambers.

Presently, implantable devices have been proposed that record IEGM signals when AF episodes are identified. However, the IEGM signals alone do not entirely reflect the true mechanical hemodynamic performance of the heart. For example, the IEGM signals may indicate that a substantial AF episode occurred, yet the episode may be of a nature in which the hemodynamic performance has not been significantly diminished from normal hemodynamic performance. Alternatively, in certain AF episodes, the corresponding IEGM signal may indicate the episode to be of nominal significance, while the underlying mechanical behavior of the heart results in substantial diminished hemodynamic performance. IMDs that record only IEGM signals do not necessarily inform a physician of the true mechanical behavior of the heart during a corresponding episode. Given the potential limited correlation between IEGM signals and mechanical hemodynamic performance, it has been difficult to assess an appropriate therapy or ablation.

A need exists for an IMD that stores information directly correlated to the hemodynamic performance of the heart during AF and atrial flutter events.

A need remains for improved techniques for implantable medical devices to detect and accurately characterize atrial fibrillation and atrial flutter.

SUMMARY

In accordance with one embodiment, a medical device is provided that comprises a lead assembly. The lead assembly includes at least one intra-cardiac (IC) electrode, an extra-cardiac (EC) electrode and a subcutaneous remote-cardiac (RC) electrode. The IC electrode is configured to be located within the heart. The EC electrode is configured to be positioned proximate to at least one of a superior vena cava (SVC) and a left ventricle (LV) of a heart. The RC electrode is configured to be located remote from the heart. An arrhythmia monitoring module is provided to analyze intra-cardiac electrogram (IEGM) signals from the at least one IC electrode to identify a potential atrial arrhythmia. An extra-cardiac impedance (ECI) module is configured to measure extra-cardiac impedance along an ECI vector between the EC and RC electrodes to obtain ECI measurements. A hemodynamic performance (HDP) assessment module is configured to determine a hemodynamic performance based on the ECI measurements. The hemodynamic performance includes one or more of cardiac output, systolic blood pressure, diastolic blood pressure, contractility, stroke volume, systolic time, Q-wave to onset of systole, and QRS to onset of systole. The arrhythmia monitoring module declares the potential atrial arrhythmia to be an atrial arrhythmia based on the hemodynamic performance determined from the ECI measurements.

The medical device may further provide the HDP assessment module to derive a current ECI waveform from current ECI measurements and compare the current ECI pattern with a prior ECI waveform that is derived form prior ECI measurements. Optionally, the HDP assessment module identifies changes in a current ECI waveform that is derived from current ECI measurements. At least a portion of the greater vessels are interposed between the RC electrode and the EC electrode such that the ECI vector extends through at least a portion of the greater vessels. Optionally, the ECI vector passes through at least a portion of at least one of the pulmonary arteries, pulmonary veins, brachiocephalic arteries and brachiocephalic veins, left carotid artery and left subclavian artery.

Optionally, the medical device further comprises a motion sensor. The arrhythmia monitoring module analyzes 3D posture movement based on an output from the motion sensor. Optionally, the arrhythmia monitoring module declares the potential atrial arrhythmia to be an atrial arrhythmia based on the 3D posture movement.

In accordance with an alternative embodiment, a method is provided for assessing hemodynamic stability. The method includes providing a lead assembly that includes at least one cardiac electrode, an EC electrode and a subcutaneous RC electrode. The cardiac electrode is configured to be located in contact with the heart. The EC electrode is configured to be positioned proximate to at least one of a superior vena cava and a left ventricle of a heart. The RC electrode is configured to be located remote from the heart. The method includes analyzing intra-cardiac electrogram signals from the at least one cardiac electrode to identify a potential atrial arrhythmia. The method includes measuring extra-cardiac impedance along an ECI vector between the EC and RC electrodes to obtain ECI measurements. The ECI vector extends through at least a portion of the greater vessels. The method further comprises determining a hemodynamic performance based on the ECI measurements and includes declaring the potential atrial arrhythmia to be an actual atrial arrhythmia based on the hemodynamic performance determined from the ECI measurements.

In accordance with one embodiment, the method further includes deriving a current ECI waveform from current ECI measurements, and comparing the current ECI waveform with a prior ECI waveform derived from prior ECI measurements. In accordance with one embodiment, the method further comprises deriving ECI waveforms from the ECI measurements and identifying changes in a current ECI waveform derived from current ECI measurements. In accordance with one embodiment, the method further comprises obtaining ventricular IEGM (V-IEGM) signals from the intra-cardiac electrogram signals from at least one cardiac electrode and measuring ST elevation from the V-IEGM signals to assess potential acute ischemia or chronic myocardial infarction.

DETAILED DESCRIPTION

Figure 1:
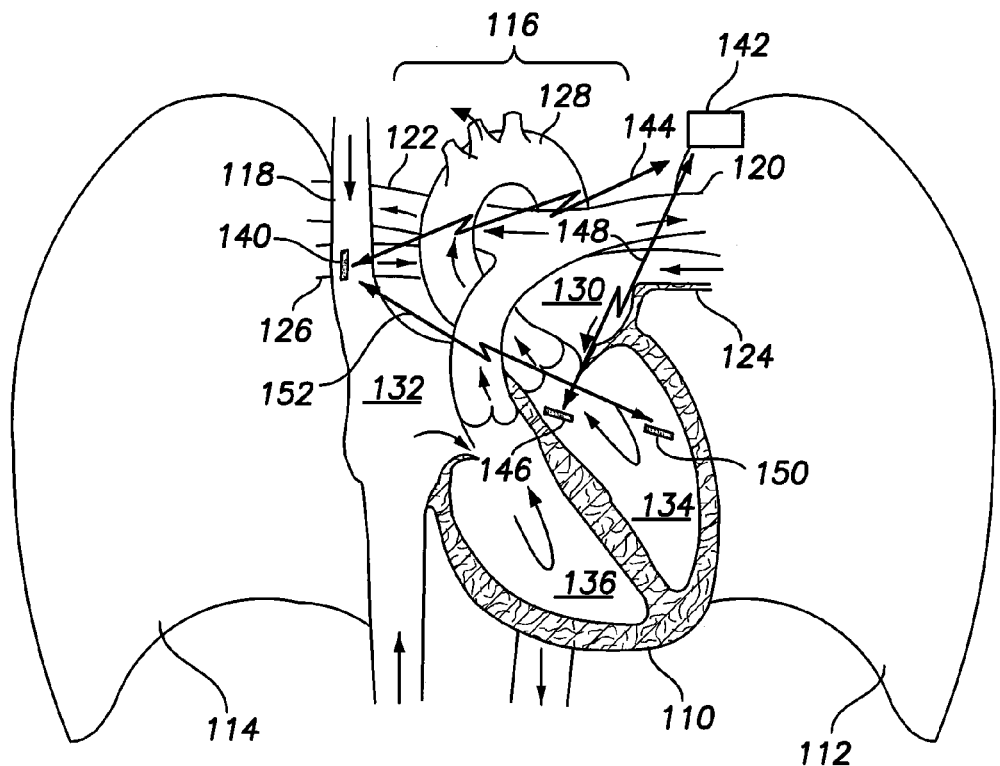
FIG. 1 illustrates a graphical representation of the upper torso of a human and illustrates various locations at which electrodes may be located outside of, but proximate to the heart, as well as at locations outside and remote from the heart in accordance with an embodiment.

In the following detailed description, reference is made to the accompanying drawings which form a part hereof, and in which are shown by way of illustration specific embodiments in which the present invention may be practiced. These embodiments, which are also referred to herein as "examples," are described in sufficient detail to enable those skilled in the art to practice the invention. It is to be understood that the embodiments may be combined or that other embodiments may be utilized, and that structural, logical, and electrical variations may be made without departing from the scope of the present invention. For example, embodiments may be used with a pacemaker, a cardioverter, a defibrillator, and the like. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

In accordance with embodiments of the present invention, hemodynamic stability is monitored through cardiogenic impedance which is used as a surrogate for hemodynamic performance. The cardiogenic impedance is analyzed during an episode of atrial fibrillation or atrial flutter. When the cardiogenic impedance confirms atrial fibrillation or atrial flutter, the system may record various waveforms and signals such as the atrial IEGM signals, the ventricular IEGM signals and corresponding hemodynamic performance waveforms during the episode. The waveforms are stored within the implantable device and subsequently transmitted to an external device for offline analysis. By saving the foregoing signals and waveforms, once an AF or atrial flutter episode has been confirmed through cardiogenic impedance, a record of the event is saved for the physician to later analyze. Otherwise, an acute AF episode may cease and a patient may recover, previously rendering it difficult for physicians to figure out what happened.

Embodiments of the present invention may derive the cardiogenic impedance from an LV-to-CAN vector which affords a good surrogate for aortic blood flow. The LV-to-CAN vector does not cross the intra-cardiac blood flow where blood flow changes beat by beat. The LV-to-CAN vector enables direct measurement of the blood flow through the aortic vessel, bypassing the intra-cardiac blood pool, and thus cardiogenic impedance measurement affords an accurate measure that is closely correlated to hemodynamic performance.

In the context of this application, the term "impedance" refers to the relatively low frequency component of the impedance. The impedance is calculated as $z=u/i$, where u is the measured voltage and i is the applied excitation current.

The term "extra-cardiac impedance" is the impedance measured between electrodes that are located outside of the four chambers of the heart. Extra-cardiac impedance is measured along an impedance vector that extends through at least a portion of the greater vessels. The "extra-cardiac impedance" may be described as having an offset generally known as Zo. Zo is typically in the range of 30 to 100 ohms. Riding on top of the offset Zo is a signal that is modulated by respiration and ejection of blood into the greater vessels, $\Delta Z$. $\Delta Z$ decreases with each systolic ejection because blood injected into the great vessels has a lower impedance that the surrounding tissue. The great vessels are juxtapositioned between the measuring electrodes. In addition, the process of breathing modulates the signal as well because the electrodes move with each breath and because air is brought into the lungs raising the impedance with each inspiration. These relatively low frequency signals may be high pass filtered at about 0.7 to reject respiration which typically has frequency components of less than 0.2 hertz while the cardiac ejections have frequency components starting at about 1 hertz to about 14 hertz. The cardiac component of $\Delta Z$ is typically in the range about 0.5 to 4% of Zo and is in the range of 0.25 to 2 ohms.

The term "hemodynamic performance" is comprised of at least one or more of cardiac output, systolic blood pressure, diastolic blood pressure, contractility, stroke volume, systolic time, Q-wave to onset of systole, QRS to onset of systole and the like.

The term "cardiac pacing conditions" includes one or more of $\Delta V$ delay, V-V delay, stimulation rate, stimulating electrodes chosen for actuating pacing, stimulation lead configuration and the like.

The term "cardiac indicator" (CI) includes extra-cardiac and intra-cardiac indicators.

FIG. 1 illustrates a graphical representation of the upper torso of a human. FIG. 1 illustrates various locates at which electrodes may be located outside of, but proximate to the heart, as well as at locations outside and remote from the heart. Electrodes are positioned at these locations to measure extra-cardiac impedance. An IMD or an external PSA analyzer then performs a hemodynamic assessment based on the impedance measurements. FIG. 1 illustrates the heart 110 between the left and right lungs 112 and 114. The direction of blood flow is noted by various arrows.

FIG. 1 also illustrates a portion of the greater vessels (generally denoted at 116) through which blood flows during entry to and exit from the heart 110. The greater vessels 116 generally include the superior vena cava (SVC) 118, the aorta 128, the pulmonary arteries 120 and 122, and the pulmonary veins 124 and 126. The greater vessels also include the left and right brachiocephalic arteries and veins, the left common carotid artery and left subclavian artery (not shown) which branch from the aorta 128. The heart 110 includes left and right atrium 130 and 132, and left and right ventricles 134 and 136.

Figure 5:
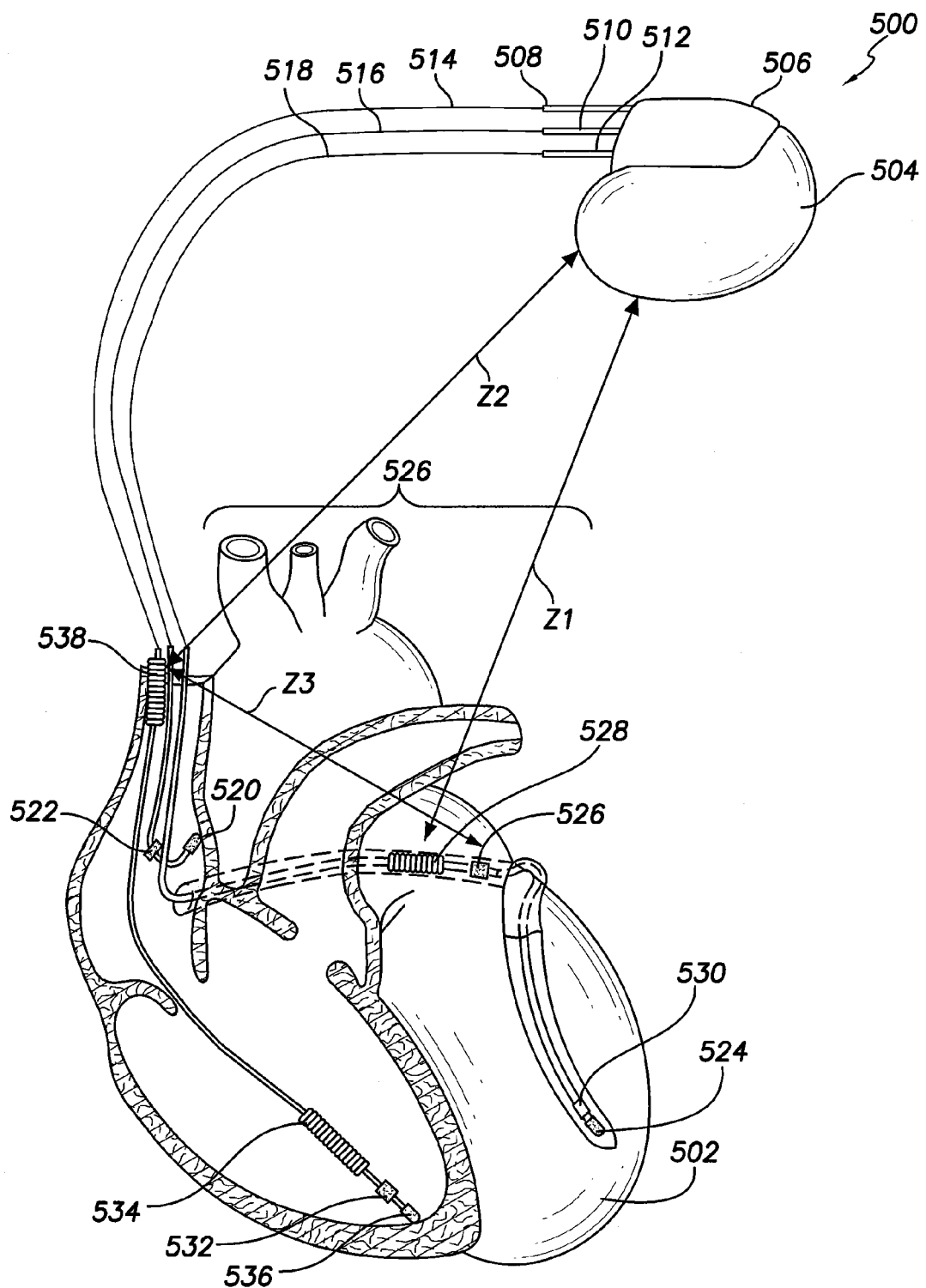
FIG. 5 illustrates an IMD that is coupled to a heart in accordance with an embodiment.

In accordance with embodiments described herein, a lead assembly of one or more leads is provided having electrodes positioned inside and outside of the heart 110. Intra-cardiac (IC) electrodes are located within one or more chambers of the heart, such as pacing, defibrillation or CRT electrodes. The IC electrodes sense IEGM signals and deliver therapies when an arrhythmia is identified that warrants therapy. Examples of IC leads and IC electrodes are shown in FIG. 5 and discussed in connection with FIGS. 5 and 6. The electrodes outside the heart are located such that at least a portion of the greater vessels 116 are interposed between the electrodes. By way of example, EC electrode may be positioned at the SVC 118, as denoted at EC electrode location 140. When an electrode is positioned at location 140, the electrode is outside of the heart 110, but proximate to the SVC 118, as well as proximate to the aorta 128, pulmonary veins 122 and pulmonary arteries 126. A second electrode may be located in a subcutaneous subclavical area, such as denoted at 142. Location 142 is remote from the heart 110 and, by way of example may correspond to the position at which an IMD is located. The housing or case of the IMD may be configured to function as an electrode to, among other things, detect impedance and/or sense cardiac activity.

Electrodes at locations 140 and 142 form an ECI vector 144 there between. The electrodes at locations 140 and 142 may be bipolar, mono-polar, tri-polar and the like. The ECI vector 144 extends through a substantial portion of the aorta 128, as well as the pulmonary veins and arteries 122 and 126, and other portions of the greater vessels 116. The ECI vector 144 may be referred to as an aorta-centric ECI vector due to the correlation of the vector 144 and the aorta 128. Electrodes at locations 140 and 142 are both outside of the four chambers 130, 132, 134 and 136 of the heart 110.

Optionally, an electrode may be located within a coronary vein that passes along the heart wall, where this electrode is positioned to be outside of, but adjacent to, the left ventricle 134. By way of example, an electrode located in the coronary vein may be positioned at location 146. When an electrode is positioned in the coronary vein proximate to the left ventricle at location 146, an ECI vector 148 may be created between electrodes at locations 142 and 146. The ECI vector 148 may be referred to as a pulmonary-centric ECI vector due to the correlation of the vector 148 and the pulmonary veins and arteries 120 and 124.

Alternatively, the electrode within the coronary vein may be shifted further along the coronary vein to a position proximate to location 150 and configured to operate with an electrode at location 140 at the SVC to form an ECI vector 152. The vectors 144, 148 and 152 substantially extend through non-cardiac tissue such that impedance variations that are detected along the vectors 144, 152 and 148 correlates closely to changes in the volume of blood flow through the greater vessels 116. As a further option, a combination of the vectors 144, 148 and 152 may be used to measure impedance. As a further option, alternative ECI vectors may be used in place of, or in combination with, the ECI vectors 144, 148 and 152.

Impedance measurements detected along ECI vectors 144, 148 and 152 closely correlate to hemodynamic performance and the mechanical behavior of the heart. In general, tissue has higher resistance than blood. During systole, blood is injected into the thoracic periphery (which includes the greater vessels). Hence, the tissue of the greater vessels between the extra-cardiac electrodes (such as at locations 140, 142, 146 and 150) becomes engorged with blood. Thus, the impedance along the ECI vectors 144, 148 and 152 decreases. During diastole, the amount of blood in the greater vessels decreases. Hence, the impedance along the ECI vectors 144, 148 and 152 increases. Impedance measurements along the ECI vectors 144, 152 and 148 increase and decrease based upon the amount of blood that is injected into the greater vessels 116.

Next, embodiments, alone or in combination with IEGM signals, are described that utilize the ECI to discriminate AF and A-Flutter and monitor patient symptoms during AF and A-Flutter episodes.

In accordance with embodiments of the present invention, processes and systems are described by which baseline ECI waveforms, HDP patterns, blood pressure and stroke volume (collectively "hemodynamic patterns") are calculated based on ECI measurements obtained during normal blood flow. The baseline hemodynamic pattern(s) of a patient is determined and compared to subsequent hemodynamic patterns from current ECI impedance measurements at various times in connection with different episodes. For example, baseline and current HDP patterns of a patient may be assessed in connection with determining whether to declare a potential atrial arrhythmia, and if so, what type of arrhythmia.

Figure 2:
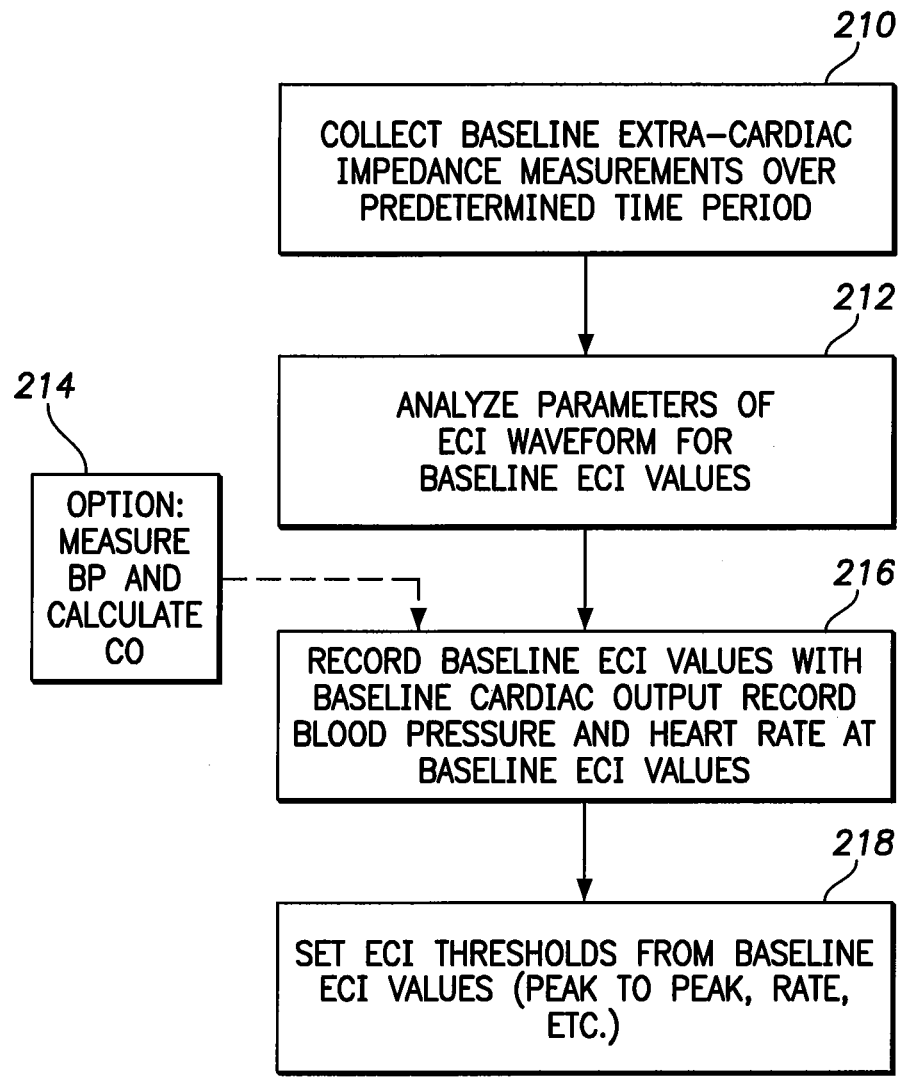
FIG. 2 illustrates a process for collecting baseline extra-cardiac impedance measurements and developing baseline parameters for subsequent use during operation and analysis of hemodynamic performance in accordance with an embodiment.

FIG. 2 illustrates a process for collecting baseline extra-cardiac impedance measurements and developing baseline parameters for subsequent use during operation and analysis of hemodynamic performance. In FIG. 2, beginning at 210, the process collects baseline ECI measurements over a predetermined period of time from two or more impedance electrodes located outside of the heart. The ECI measurements are taken in connection with an ECI vector that extends through at least a portion of the greater vessels surrounding the heart.

Figure 3:
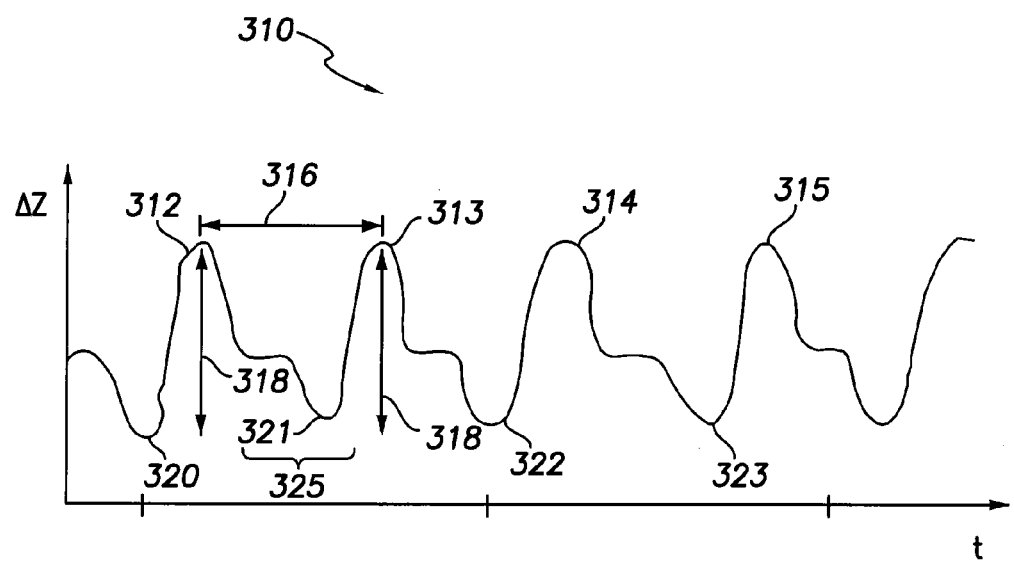
FIG. 3 illustrates a baseline ECI waveform produced from ECI measurements over a predetermined time period in accordance with an embodiment.

FIG. 3 illustrates a baseline ECI waveform 310 produced from ECI measurements over a predetermined time period. The ECI waveform 310 is associated with a normal heart having no arrhythmia and exhibiting a physiologic (healthy) hemodynamic performance pattern or behavior over time. The ECI waveform 310 is shown for a series of four cardiac cycles, but may be longer or shorter. The vertical axis in the graph of FIG. 3 corresponds to an impedance difference $\Delta Z$. Consistent with impedance cardiography, the axis for $\Delta Z$ represents a decrease in impedance when moving upward. Therefore, the abscissa is inverted. The ECI waveform 310 includes peaks 312-315 that are generally evenly spaced from one another by an interval 316. Each of the peaks 312 has peak to peak amplitude 318 between the positive peaks 312-315 and the preceding corresponding minimal peaks (valleys) 320-323. In the example of FIG. 3, the peak to peak amplitudes or distances 318 are substantially similar for each heart cycle. A bracket 325 denotes the interval between the peaks 312 and 313. During normal cardiac behavior, the waveform pattern of $\Delta Z$ within the region 325 may exhibit relatively small changes in amplitude with no or few shifts in the slope or direction of $\Delta Z$. It should be realized that the intervals 316 may not be the same and the peak to peak amplitudes 318 may not be the same, yet the heart may still be healthy and exhibiting a normal hemodynamic performance. The waveform 310 is also modulated by breathing because the intra-thoracic pressure changes. These minor changes may be averaged out over several respiratory cycles or the signals may be sampled with the peaks and valleys identified on the respiratory component of the $\Delta Z$ waveform. Either method is useful for working with the respiratory variations in the cardiac $\Delta Z$ waveform.

Returning to FIG. 2, once the ECI waveform 310 is obtained at 210, flow moves to 212. At 212, the process analyzes a predetermined set of parameters associated with the ECI waveform 310 to determine baseline ECI values. The baseline ECI values are used to define desired characteristics of a baseline ECI waveform or pattern. By way of example, the parameters may correspond to i) the peak to peak amplitude 318, ii) the interval 316, iii) the number of slope changes within the inter-peak region associated with bracket 325 and the like. The parameters may also include a measure of the regularity or stability of the ECI waveform or waveform. The regularity represents the symmetry within the waveform for successive heart cycles. For example, the symmetry may be based on whether adjacent peaks or a series of peaks are separated by intervals 316 that are within a desired range from one another. The symmetry may be based on whether the intervals 316 are generally equal in length and/or fall within interval threshold limits. The symmetry may be based on whether the peak to peak amplitudes are within a desired range from one another, or are generally equal, and/or fall within peak to peak amplitude threshold limits. A combination of the above factors may be used, as well as other factors, to measure the regularity of an ECI waveform.

Once the baseline ECI values are obtained at 212, the baseline ECI values are recorded at 216 along with any other baseline information related to hemodynamic performance. For example, an optional operation may be provided at 214 where the blood pressure is directly measured and hemodynamic performance calculated. When the blood pressure is measured at 214, the blood pressure may be recorded at 216 along with the corresponding baseline ECI values. At 216, the heart rate at the baseline ECI values may also be recorded.

Next, at 218, ECI thresholds are set based upon the baseline ECI values. ECI thresholds may represent limits that, when exceeded, are indicative of unduly low or otherwise unacceptable hemodynamic performance. For example, when the peak to peak distance or amplitude is measured during a normal heart cycle, a peak to peak (P-P) threshold may be set as a percentage of the normal or baseline peak to peak amplitude. Thereafter, when a subsequently measured ECI waveform exhibits P-P amplitude that falls below the baseline P-P amplitude by more than the ECI threshold, the hemodynamic performance may be deemed too low or insufficient. As a further option, a regularity threshold may be established in which peaks in the ECI waveform must occur within some percentage of the baseline regularity. Otherwise, the system may determine that insufficient hemodynamic performance is being delivered and therapy is warranted. The ECI thresholds and baseline ECI values are used in various applications and systems as described hereafter.

Embodiments are described herein, whereby impedance is measured along various ECI vectors to detect changes in the impedance of the greater vessels around the heart. Optionally, the changes in impedance may be recorded as one or more impedance profiles reflecting changes in impedance along one or more ECI vectors over the cardiac cycle. The impedance profile(s) may be used to access hemodynamic performance, such as cardiac output over one or more cardiac cycles. The hemodynamic performance represents an amount (e.g. in ml) of blood output by the heart per unit of time (e.g. per minute). For example, if an individual's stroke volume is 20 ml/stroke and the heart rate was 60 beats per minute, then the hemodynamic performance would be 120 ml/minute. The hemodynamic performance is a function of the change in impedance $\Delta Z$ along an ECI vector. For example, the hemodynamic performance (HDP) is proportional to $\Delta Z$ times the mechanical heart rate (also referred to as the pulse rate). Embodiments calculate HDP based on the $\Delta Z$ and mechanical HR.

Figure 4:
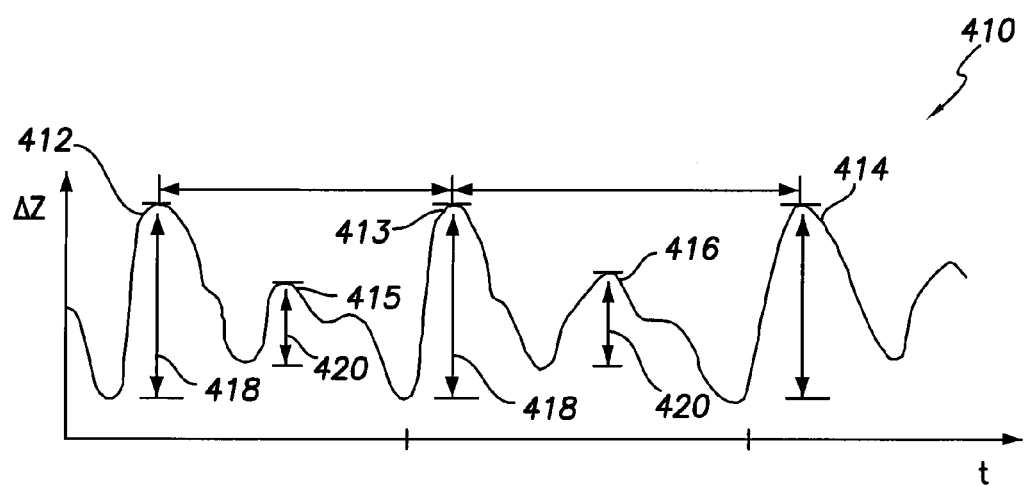
FIG. 4 illustrates an example of an ECI waveform or pattern that may produce inferior hemodynamic performance in accordance with an embodiment.

FIG. 4 illustrates an example of an ECI waveform E10 that may be collected as a current ECI measurement during pathologic or abnormal hemodynamic performance. In FIG. 4, the ECI waveform 410 exhibits a known pathologic pattern referred to as an "alternan". The "alternan" hemodynamic performance is characterized by the repetitive pattern of a series of large peaks 412-414 that are separated by smaller local peaks 415 and 416. When the current ECI waveform 410 is collected, it is analyzed, and the peak to peak amplitude 418 is measured for certain peaks (e.g. 412 and 413). A smaller peak to peak amplitude 420 will be measured in connection with the local peaks 415 and 416 and identified to occur between the larger peaks 412-414. When this repetitive pattern of larger and smaller peaks is identified, it is classified as alternan hemodynamic performance which is abnormal.

Figure 9:
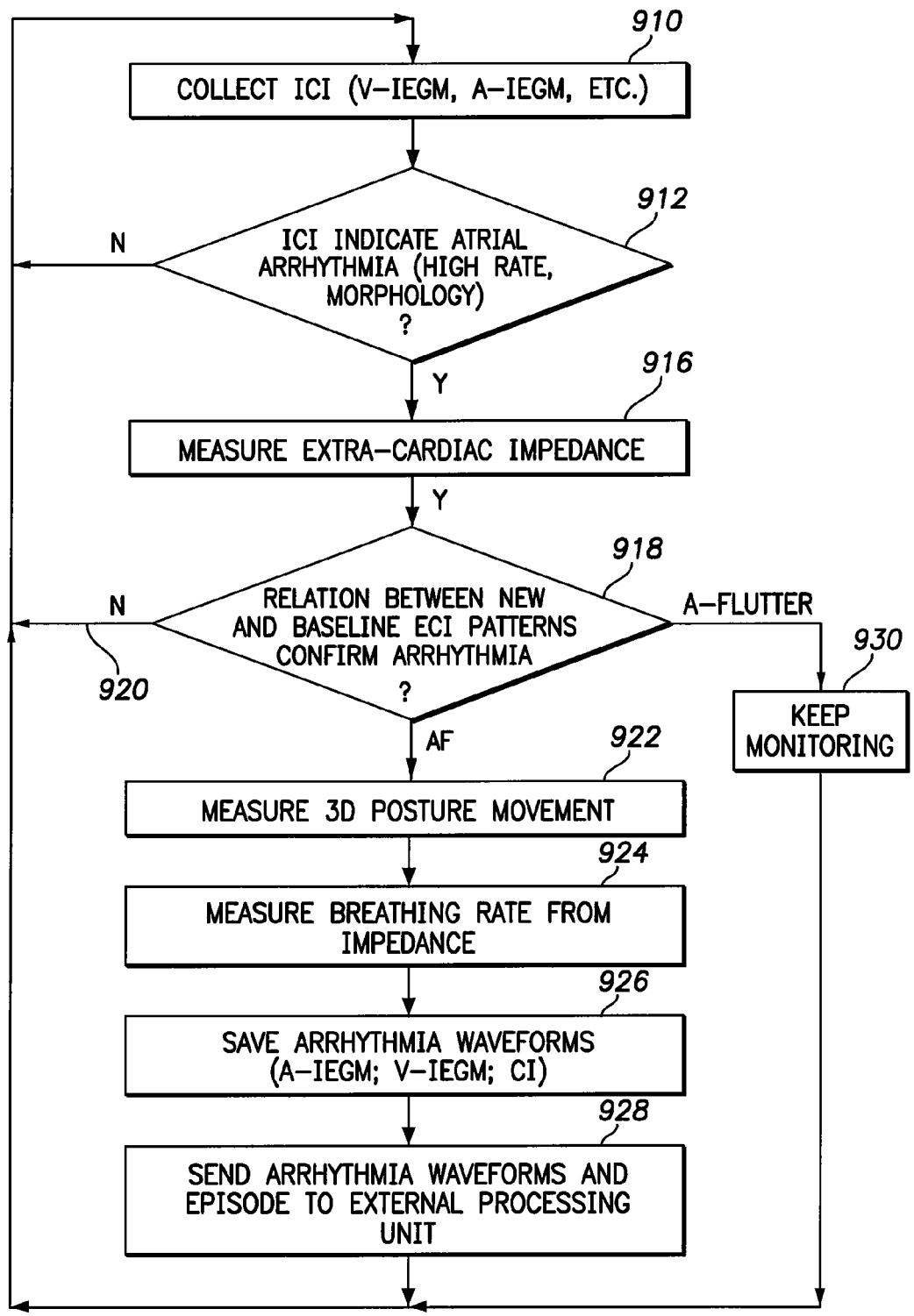
FIG. 9 illustrates a process carried out in accordance with an embodiment to discriminate and monitor patient symptoms indicative of atrial fibrillation and/or atrial flutter through the use of cardiogenic impedance as a confirmation analysis.

FIG. 9 illustrates a process carried out in accordance with an embodiment to discriminate and monitor patient symptoms indicative of atrial fibrillation and/or atrial flutter through the use of cardiogenic impedance as a confirmation analysis. Beginning at 910, the IMD or external device collects intra-cardiac electrogram (IEGM) signals from an electrode configuration with at least one cardiac electrode in contact with the heart. The IEGM signals may be ventricular or atrial. At 912, the IEGM signals are analyzed to determine whether the IEGM signals are indicative of atrial fibrillation, an atrial arrhythmia, such atrial flutter and the like. The analysis at 912 may determine whether the heart rate is above an AF rate threshold, or the heart rate is above an A-Flutter threshold. For example, the rate within the atrium may be analyzed to determine whether the atrial rate exceeds one or more predetermined thresholds. Optionally, other characteristics of the IEGM signals may be analyzed, such as P-wave shape, T-wave shape, P-wave timing/absence, ST elevation and other morphology indicators. When the intra-cardiac electrograms are not indicative of AF or A-Flutter, flow passes back to 910 to collect new IEGM signals. However, when at 912 the atrial rate exceeds the one or more predetermined thresholds, flow moves to 916 to begin a cardiogenic impedance based confirmation process.

At 916, the IMD or external device detects cardiogenic impedance from a configuration of EC and RC electrodes that form one or more ECI vectors passing through the greater vessels. The collecting at 910 and ECI measurements at 916 may be for a simple cardiac cycle or for a series of cardiac cycles. Once ECI measurements are collected for a predetermined period of time, flow moves to 918 where the current ECI waveform collected at 916 is compared with a previously acquired baseline ECI waveform. When the current and baseline ECI waveforms correlate with one another by an amount within a predetermined correlation threshold, then it is determined at 918 that AF or A-Flutter is not confirmed. Instead, it is determined that sufficient hemodynamic performance exists. Hence, flow passes along 920 back to 910. When the current ECI waveform diverges sufficiently from the baseline ECI waveform, this non-correlation may be an indication of insufficient hemodynamic performance depending upon the degree of non-correlation. The degree on non-correlation between current and baseline ECI waveforms may be quantified as a percentage, such as 20% non-correlation, 50% non-correlation, 80% correlation, etc. The degree of non-correlation, in combination with the heart rate detected by the IEGM signals, may be used to discriminate between AF and A-Flutter. For example, 70% correlation (30% non-correlation) and a heart rate between 90 and 160 bpm may be indicative of A-Flutter. Alternatively, 30% correlation (70% non-correlation) and a heart rate above 160 bpm may be indicative of AF. Hence, when the relation between the current and baseline ECI signals differs sufficiently in a predetermined manner, AF or A-Flutter is confirmed at 918. When the process confirms a potential AF at 918, flow moves to 922. When the process confirms a potential A-Flutter, flow moves to 930. In the example of FIG. 9, flow diverges at 918 depending upon whether a potential AF or a potential A-Flutter was being confirmed (to 922 or 930). Optionally, the operations at 922 to 928 may be performed when actual AF or A-Flutter are declared to occur.

At 922, the IMD measures the three dimensional posture movement of the patient. At 922, the system analyzes three dimensional posture movement to determine prior patient activity such as whether the patient abruptly switched to a horizontal position and has remained stationary for a predetermined number of seconds (e.g. 10 or 30 seconds) which may be indicative of fainting. Alternatively, the movement and posture or orientation of the patient may be analyzed for a preceding period of time (e.g. the last 10 seconds, 30 seconds or 1 minute) to determine whether the patient's behavior is associated with behavior indicative of AF or A-Flutter, or simply exercise. An accelerometer or motion detector may be used to measure the 3D posture movement to determine if the patient is oriented horizontal or standing up. The motion detector may be used to determine whether the patient is moving, and if not, how long it has been since the patient has last moved (e.g., 10 sec., 30 sec.). A horizontal position and/or lack of motion may indicate that the patient has fainted or is otherwise unconscious.

At 924, the system measures the breathing rate of the patient. The breathing rate may be determined by impedance measurements, motion signals, and the like. At 926, the hemodynamic parameters and values are saved in a portion of memory for longer term storage. The information saved may include, among other things, the AF or A-Flutter waveform (such as acquired through an atrial IEGM, a ventricular IEGM, from the ECI measurements and the like). At 928, the system transmits the saved hemodynamic information, IEGM signals, AF waveform and episode information to an external processing unit.

Figure 10:
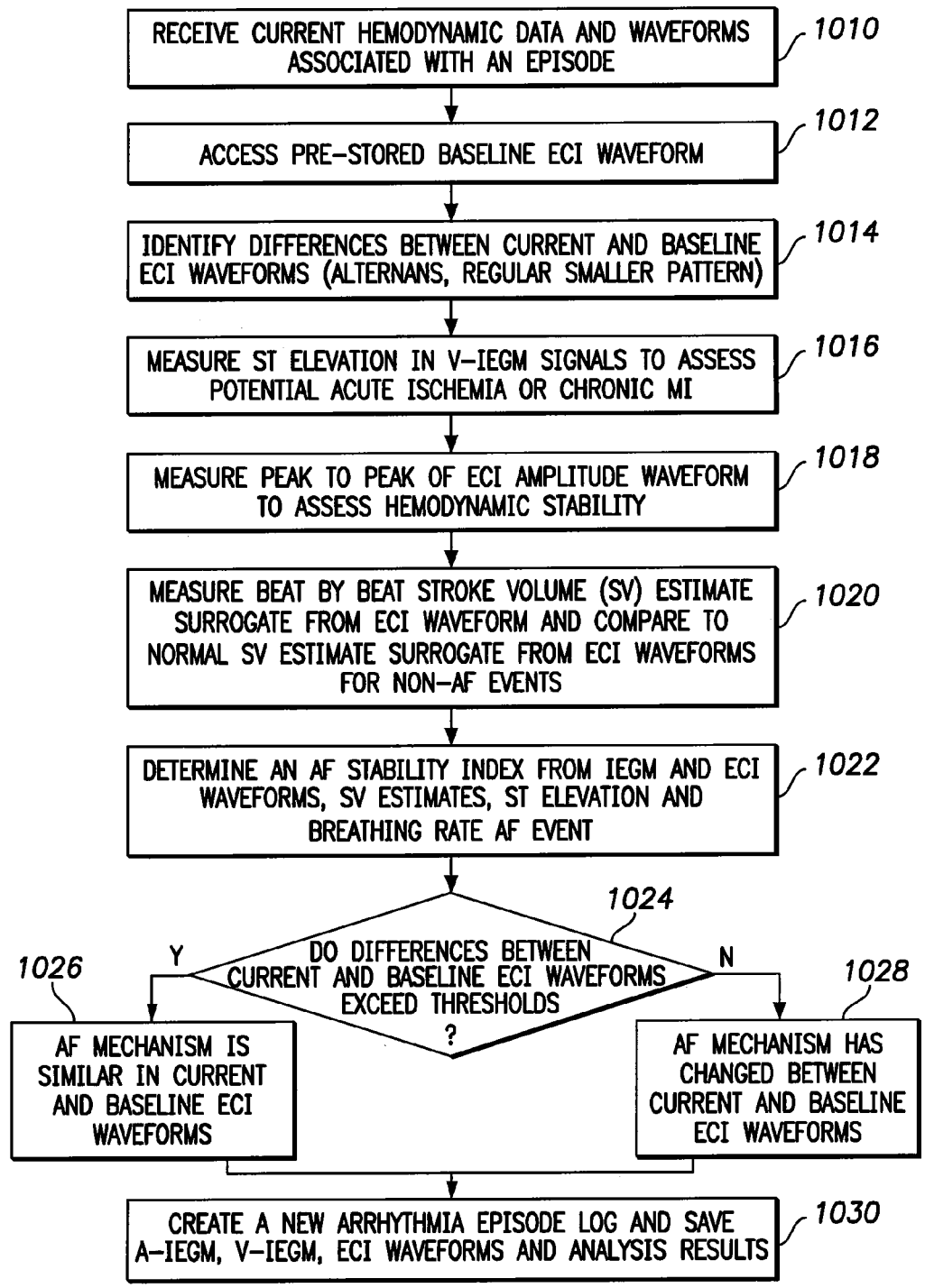
FIG. 10 illustrates a process carried out by one of an implantable device and an external programmer to analyze AF and A-Flutter episodes.

FIG. 10 illustrates a process carried out by one of an implantable device and an external programmer to analyze AF and A-Flutter episodes. Beginning at 1010, the process receives a current ECI waveform associated with an episode of interest. The current ECI waveform may represent a waveform over a predetermined period of time corresponding to the change in cardiogenic impedance. The current ECI waveform may be for a single cardiac cycle or an ensemble average for a series of cardiac cycles. At 1012, access is obtained to a baseline or pre-stored ECI waveform is obtained from memory. The baseline ECI waveform may be obtained as a baseline during a time when the patient is not experiencing AF or A-Flutter. The background ECI waveform may be for a predetermined of time or may be created from an average of multiple ECI waveforms obtained at different times, each of which are associated with normal rhythmic cardiac behavior. The baseline ECI waveform may be from the present patient, from a group of patients or may be a simulated pattern not from actual patients.

At 1014, the process identifies differences between the current ECI waveform and the baseline ECI waveform. For example, the differences may be obtained through an autocorrelation technique and the like. The identification at 1014 may also include analysis of the current ECI waveform alone or in combination with a baseline ECI waveform in an effort to identify alternates or other predefined waveform patterns known to be associated with AF or A-Flutter. At 1016, the ventricular IEGM signals are analyzed to obtain ST elevations within the IEGM signals. ST elevations are accessed to determine whether potential acute ischemia or a chronic myocardial infarction (MI) exists.

At 1018, the current ECI waveform is analyzed to identify peaks and valleys within the waveform. The peaks of the ECI waveform are compared and the valleys of the ECI waveform are compared in an effort to determine whether there are progressive trends in the ECI waveform. For example, the amplitude of the ECI waveform may progressively decrease. Alternatively, the amplitude of the ECI waveform may remain steady, yet the area under each peak within the ECI waveform may decrease. These changes in the shape of the ECI waveform may be indicative of AF or A-Flutter.

At 1020, the process measures the beat by beat stroke volume during the episode. The stroke volume (SV) may be indirectly calculated through the ECI waveform which may be utilized as a surrogate for stroke volume. Once the beat by beat stroke volume is calculated from the ECI waveform, the current stroke volume is compared to a previously acquired stroke volume that was acquired during a normal non-AF episode. Comparing the current stroke volume to a previous normal stroke volume enables the system to better characterize AF episodes and A-Flutter episodes as valid or incorrect.

At 1022, an AF stability index is determined from the above discussed waveforms and parameters, such as from the IEGM and ECI waveforms, the stroke volume measurements, the ST elevation and the breathing rate during the AF episode. At 1024, it is determined whether differences between current and baseline ECI waveforms exceed corresponding thresholds. If the threshold(s) are exceeded, flow moves to 1026. Otherwise flow moves to 1028. At 1026, the AF mechanism is similar in the current and baseline ECI waveforms. At 1028, the AF mechanism is not similar in the current and baseline ECI waveforms. At 1030, a new arrhythmia episode log is created and the method saves A-IEGM, V-IEGM, and ECI waveforms and any analysis results.

FIG. 5 illustrates an IMD 500 or external device, such as PSA, that is coupled to a heart 502. The external device may be connected to leads such as during implantation of an IMD in accordance with the processes described herein to determine a preferred therapy and lead position based on hemodynamic performance. The IMD 500 may be a cardiac pacemaker, an ICD, a defibrillator, an ICD coupled with a pacemaker, and the like, implemented in accordance with one embodiment of the present invention. The IMD 500 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings. In accordance with the processes explained herein, the IMD 500 may be controlled to detect IEGM signals and ECI measurements and based thereof, to identify potential atrial arrhythmias and insufficient hemodynamic performance.

The IMD 500 includes a housing 504 that is joined to a header assembly 506 (e.g., an IS-4 connector assembly) that holds receptacle connectors 508, 510, 512 that are connected to a right ventricular lead 514, a right atrial lead 516, and a coronary sinus lead 518, respectively. The leads 514, 516, and 518 may be located at various locations, such as an atrium, a ventricle, or both to measure the physiological condition of the heart 502. One or more of the leads 514, 516, and 518 detect IEGM signals that form an electrical activity indicator of myocardial function over multiple cardiac cycles. To sense atrial cardiac signals and to provide right atrial chamber stimulation therapy, the right atrial lead 516 has at least an atrial tip electrode 520, which typically is implanted in the right atrial appendage, and an atrial ring electrode 522. The IEGM signals represent analog signals that are subsequently digitized and analyzed to identify waveforms or segments of interest. Examples of waveforms or segments of interest identified from the IEGM signals include the P-wave, T-wave, the R-wave, the QRS complex, the ST segment, and the like. The waveforms of interest may be collected over a period of time.

The coronary sinus lead 518 receives atrial and ventricular cardiac signals and delivers left ventricular pacing therapy using at least a left ventricular ("LV") tip electrode 524, and delivers left atrial ("LA") pacing therapy using at least a left atrial ring electrode 526. The coronary sinus lead 518 also is connected with a LV ring electrode 530 disposed between the LV tip electrode 524 and the left atrial ring electrode 526. The LV ring electrode 530 may be used as a defibrillation electrode. The right ventricular ("RV") lead 514 has an RV tip electrode 536, an RV ring electrode 532, an RV coil electrode 534, and an SVC coil electrode 538. The RV lead 514 is capable of receiving cardiac signals, and delivering stimulation in the form of pacing, CRT and shock therapy to the right ventricle. The RV coil electrode 534 may be used as a defibrillation electrode. The housing 504 may also function as an electrode.

The IMD 500 measures ECI impedance parameters to monitor and determine variations in the hemodynamic performance in accordance with the processes explained herein. An impedance parameter includes an impedance vector that represents the impedance measured along a path (generally a linear path) between at least two points. One or more impedance vectors measured by the IMD 500 may extend through the greater vessels 526. The impedance vectors that extend through the greater vessels 526 represent the impedance of the tissue and the blood along the paths of the impedance vectors. The IMD 500 may determine the average of an impedance vector for a number of cardiac cycles and compare multiple averages. In a healthy heart 502, the average impedance vector over time may remain approximately the same over multiple sets of cardiac cycles.

By way of example only, the impedance vectors measured by the IMD 500 may include one or more of first, second and third ECI impedance vectors Z1, Z2 and Z3 (FIG. 5). The first and second ECI impedance vectors Z1 and Z2 are between the housing 504 and SVC coil electrode 538 and the housing 504 and LA electrode 528, respectively. The third ECI impedance vector Z3 is between the LA ring electrode 526 and SVC coil electrode 538.

The IMD 500 may calculate one or more of the impedance vectors using a four terminal measurement technique in one embodiment. The four terminal measurement technique may reduce the impact that the intrinsic impedance of the electrodes has on the impedance vector. The intrinsic impedances of the electrodes 524-538 may be large when compared to the change $\Delta Z$ in the impedance of the greater vessels. For example, the LV and RV electrode tips 524, 536 may have intrinsic impedances of 500 ohms or more while the change $\Delta Z$ in impedance of the myocardium in the greater vessels may be approximately 50 ohms or less. The four terminal measurement technique can eliminate the intrinsic impedances of the electrodes from the measured impedance vector.

The four terminal measurement technique involves applying a current across a predetermined combination of the electrodes while measuring a voltage between a different combination of the electrodes. As shown in FIG. 5, the current may be supplied between the RV coil electrode 534 and the LV ring electrode 530. The voltage is measured between the SVC coil 538 and housing 504. The voltage represents the voltage difference measured. Using the voltage and the current, the impedance vector may be calculated.

Figure 6:
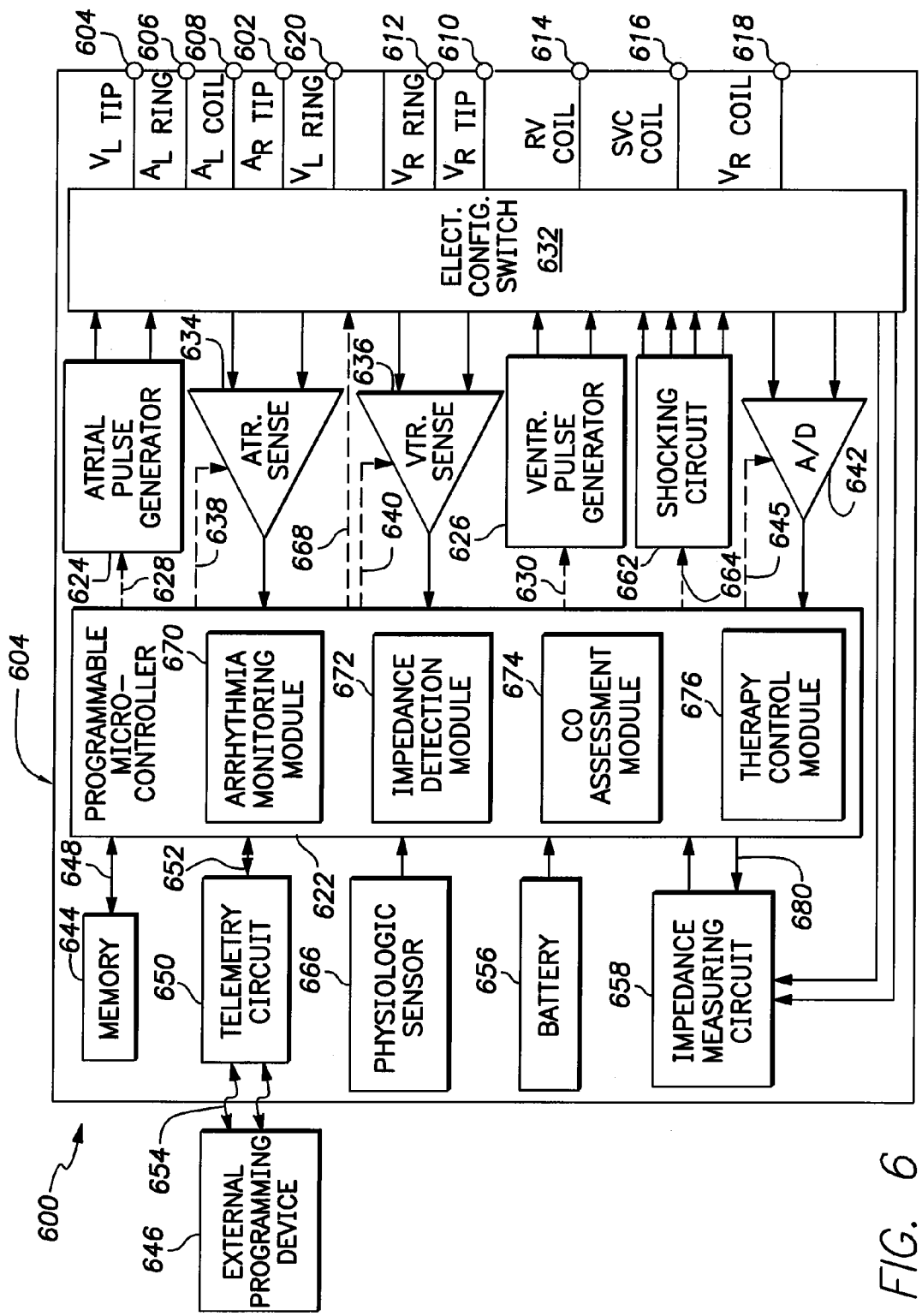
FIG. 6 illustrates a block diagram of exemplary internal components of an IMD that may be implemented in accordance with an embodiment.

FIG. 6 illustrates a block diagram of exemplary internal components of the IMD 500. The IMD 500 is for illustration purposes only, and it is understood that the circuitry could be duplicated, eliminated or disabled in any desired combination to provide a device capable of treating the appropriate chamber(s) of the heart with cardioversion, CRT defibrillation and/or pacing stimulation. The housing 504 for IMD 500 (shown schematically in FIG. 6), is often referred to as the "can", "case" or "case electrode" and may be programmably selected to act as the return electrode for all "unipolar" modes. The housing 504 further includes a connector (not shown) having a plurality of terminals, namely a right atrial tip terminal (AR TIP) 602, a left ventricular tip terminal (VL TIP) 604, a left atrial ring terminal (AL RING) 606, a left atrial shocking terminal (AL COIL) 608, a right ventricular tip terminal (VR TIP) 610, a right ventricular ring terminal (VR RING) 612, a right ventricular shocking terminal (RV COIL) 614, an SVC shocking terminal (SVC COIL) 616, a right ventricular coil terminal (VR COIL) 618 and a left ventricular ring terminal (VL RING) 620.

The IMD 500 includes a programmable processor module 622, which controls the operation of the IMD 500 based on acquired cardiac signals and impedance vectors. The processor module 622 (also referred to herein as a processor module or unit) typically includes a microprocessor, or equivalent control circuitry, is designed specifically for controlling the delivery of stimulation therapy and may further include RAM or ROM memory, logic and timing circuitry, state machine circuitry, and I/O circuitry. Typically, the processor module 622 includes the ability to process or monitor input signals (e.g., data) as controlled by a program code stored in a memory. Among other things, the processor module 622 receives, processes, and manages storage of digitized data from the various electrodes 504, 524-538 (shown in FIG. 5). The processor module 622 may also analyze the data, for example, in connection with collecting, over a period of time, variations in a segment of interest, ECI measurements and impedance vectors. For example, the processor module 622 monitors variations in one or more of segments of interest such as the ST segment and the R-wave and variations in hemodynamic performance and impedance vectors.

The modules in the processor module 622 that monitor arrhythmias and HDP include an arrhythmia monitoring module 670, the impedance detection module 672, a HDP assessment module 674 and a therapy module 676. The arrhythmia monitoring module 670 determines segment variations such as ST segment variations and changes in the amplitude and rate of the R-wave to identify arrhythmias. The arrhythmia monitoring module 670 analyzes intra-cardiac electrograms from cardiac electrodes to identify a potential atrial arrhythmia. For example, a potential atrial arrhythmia may be identified when the heart rate exceeds AF or A-Flutter thresholds (e.g. greater than 90 for A-Flutter and greater than 160 for AF). Alternatively, a potential atrial arrhythmia may be identified based on the morphology of the IEGM signal. The impedance detection module 672 measures and/or calculates one or more of the first, second and third ECI impedance vectors Z1, Z2 and Z3.

The HDP assessment module 674 monitors the HDP condition based on changes in the impedance vectors monitored by the impedance detection module 672. When the HDP is below one or more thresholds, the arrhythmia monitoring module 670 may declare the potential atrial arrhythmia to be an actual atrial arrhythmia. For example, the arrhythmia monitoring module 672 may declare an actual atrial arrhythmia to be AF when the heart rate is above an AF rate threshold and the current and baseline ECI waveforms correlate by less than a correlation AF threshold (e.g., less than 30% correlation). The arrhythmia monitoring module 672 may declare A-Flutter when the heart rate is between A-Flutter and AF rate thresholds (e.g., 90-160) and the current and baseline ECI waveforms correlate by less than a correlation A-Flutter threshold (e.g., at least 30% correlation).

The therapy control module 676 assesses and determines what therapy to deliver. The therapy control module 676 declaring ICI based therapies, IEGM based therapies and ECI based therapies. The therapy control module 676 over-ruling and confirming ICI based therapy and non-therapy judgments utilizing ECI and/or HDP information.

Optionally, the HDP assessment module 674 identifies changes in a current ECI waveform that is derived from current ECI measurements. For example, the HDP assessment module 674 may derive a current ECI waveform from current ECI measurements and compare the current ECI pattern with a prior ECI waveform that is derived form prior ECI measurements. The arrhythmia monitoring module 670 is configured to analyze 3D posture movement based on an output from the motion sensor. The arrhythmia monitoring module 670 is configured to declare the potential atrial arrhythmia to be an atrial arrhythmia based on the 3D posture movement. The physiologic sensor 666 may be used as a breathing rate sensor. The arrhythmia monitoring module 670 is configured to analyze a breathing rate based on an output from the physiologic sensor 666. The HDP assessment module 674 is configured to analyze parameters associated with the ECI measurements relative to ECI thresholds to determine whether sufficient hemodynamic performance exists. The memory 644 is configured to store baseline ECI values associated with baseline ECI measurement obtained when normal hemodynamic performance is present. The HDP assessment module 674 utilizing the baseline ECI values to analyze current ECI measurements to determine whether sufficient hemodynamic performance exists. The therapy control module 676 is configured to determine whether to apply a corrective therapy based on the ECI measurements and the IEGM signals. The HDP assessment module 674 determines whether hemodynamic performance is hemodynamically stable or unstable based on the ECI measurement. The therapy control module 676 may suspend an IEGM based therapy when the ECI measurements indicate that the hemodynamic performance is hemodynamically stable.

The IMD 500 includes an atrial pulse generator 624 and a ventricular/impedance pulse generator 626 to generate pacing stimulation pulses. In order to provide stimulation therapy in each of the four chambers of the heart, the atrial and ventricular pulse generators 624 and 626, may include dedicated, independent pulse generators, multiplexed pulse generators, or shared pulse generators. The pulse generators, 624 and 626, are controlled by the processor module 622 via appropriate control signals, 628 and 630, respectively, to trigger or inhibit the stimulation pulses.

Switch 632 includes a plurality of switches for connecting the desired electrodes, including the electrodes 504 and 524 through 138, to the appropriate I/O circuits, thereby providing complete electrode programmability. The switch 632, in response to a control signal J68 from the processor module 622, determines the polarity of stimulation pulses (e.g., unipolar, bipolar, etc.) by selectively closing the appropriate combination of switches (not shown) as is known in the art. Atrial sensing circuits 634 and ventricular sensing circuits 636 may also be selectively coupled to the leads 514, 516 and 518 through the switch 632 for detecting the presence of cardiac activity in each of the four chambers of the heart 502. Control signals 638 and 640 from processor module 622 direct output of the atrial and ventricular sensing circuits 634 and 636 that are connected to the processor module 622. In this manner, the atrial and ventricular sensing circuits 634 and 636 are able to trigger or inhibit the atrial and ventricular pulse generators 624 and 626.

The cardiac signals are applied to the inputs of an analog-to-digital (ND) data acquisition system 642. The data acquisition system 642 is configured to acquire IEGM signals, convert the raw analog data into a digital IEGM signals, and store the digital IEGM signals in a memory 644 for later processing and/or telemetric transmission to an external device 646.

A control signal 645 from the processor module 622 determines when the ND 642 acquires signals, stores them in memory 644, or transmits data to the external device 646. The ND 642 is coupled to the right atrial lead 516 (shown in FIG. 1), the coronary sinus lead 518 (shown in FIG. 1), and the right ventricular lead 514 through the switch 632 to sample cardiac signals across any combination of desired electrodes 524-538 (shown in FIG. 1). The processor module 622 is coupled to the memory 644 by a suitable data/address bus 648, wherein the programmable operating parameters used by the processor module 622 are stored and modified, as required, in order to customize the operation of IMD 500 to suit the needs of a particular patient. The memory 644 may also store data indicative of myocardial function, such as the IEGM data, ST segment shifts, reference ST segment shifts, ST segment shift thresholds, R wave amplitudes, R wave amplitude changes, impedance vectors, HDP patterns/waveforms, ECI waveforms/waveforms, blood pressure, stroke volume, trend information associated with ischemic episodes, and the like for a desired period of time (e.g., 6 hours, 12 hours, 18 hours or 24 hours, and the like).

The operating parameters of the IMD 500 may be non-invasively programmed into the memory 644 through a telemetry circuit 650 in communication with the external device 646, such as an external device 700 (shown in FIG. 7), a trans-telephonic transceiver or a diagnostic system analyzer. The telemetry circuit 650 is activated by the processor module 622 by a control signal 652. The telemetry circuit 650 allows intra-cardiac electrograms, ECI, HDP, BP, SV data and status information relating to the operation of IMD 500 (as contained in the processor module 622 or memory 644), to be sent to the external device 646 through an established communication link 654. The IMD 500 additionally includes the battery 656, which provides operating power to all of the circuits shown within the housing 504, including the processor module 622. The IMD 500 also includes a physiologic sensor 666 that may be used to adjust pacing stimulation rate according to the exercise state of the patient.

In the case where IMD 500 is intended to operate as an ICD device, the IMD 500 detects the occurrence of an arrhythmia, confirms insufficient HDP and automatically applies an appropriate electrical shock therapy to the heart aimed at terminating the detected arrhythmia. To this end, the processor module 622 further controls a shocking circuit 662 by way of a control signal 664. The shocking circuit 662 generates shocking pulses of low (up to 0.5 joules), moderate (0.5-10 joules) or high energy (11 to 40 joules). Such shocking pulses are applied to the heart 502 (shown in FIG. 5) of the patient through at least two shocking electrodes, and as shown in this embodiment, selected from the left atrial coil electrode 528 (shown in FIG. 1), the RV coil electrode 534 (shown in FIG. 5), and/or the SVC coil electrode 538 (shown in FIG. 5). When the IMD operates as a pacemaker, the processor module applies a therapy using cardiac pacing conditions associated with the preferred hemodynamic performance based on the EC measurements (as discussed below in more detail in connection with FIGS. 12 and 13). The processor module compares the EC measurements to determine a preferred hemodynamic performance based on the EC measurements. The processor module applies a therapy using cardiac pacing conditions associated with the preferred hemodynamic performance based on the stored EC measurements.

The IMD 500 includes an impedance measuring circuit 658 which is enabled by the processor module 622 via a control signal 660. Alternatively, the ECI impedance measuring circuit 658 is included in the impedance detection module 672. The ECI impedance measuring circuit 658 is advantageously coupled to the switch 632 so that impedance at any desired electrode may be obtained. For example, the ECI impedance measuring circuit 658 may measure impedance vectors between predetermined combinations of the electrodes to monitor hemodynamic performance and determine whether sufficient or insufficient HDP exists.

Figure 7:
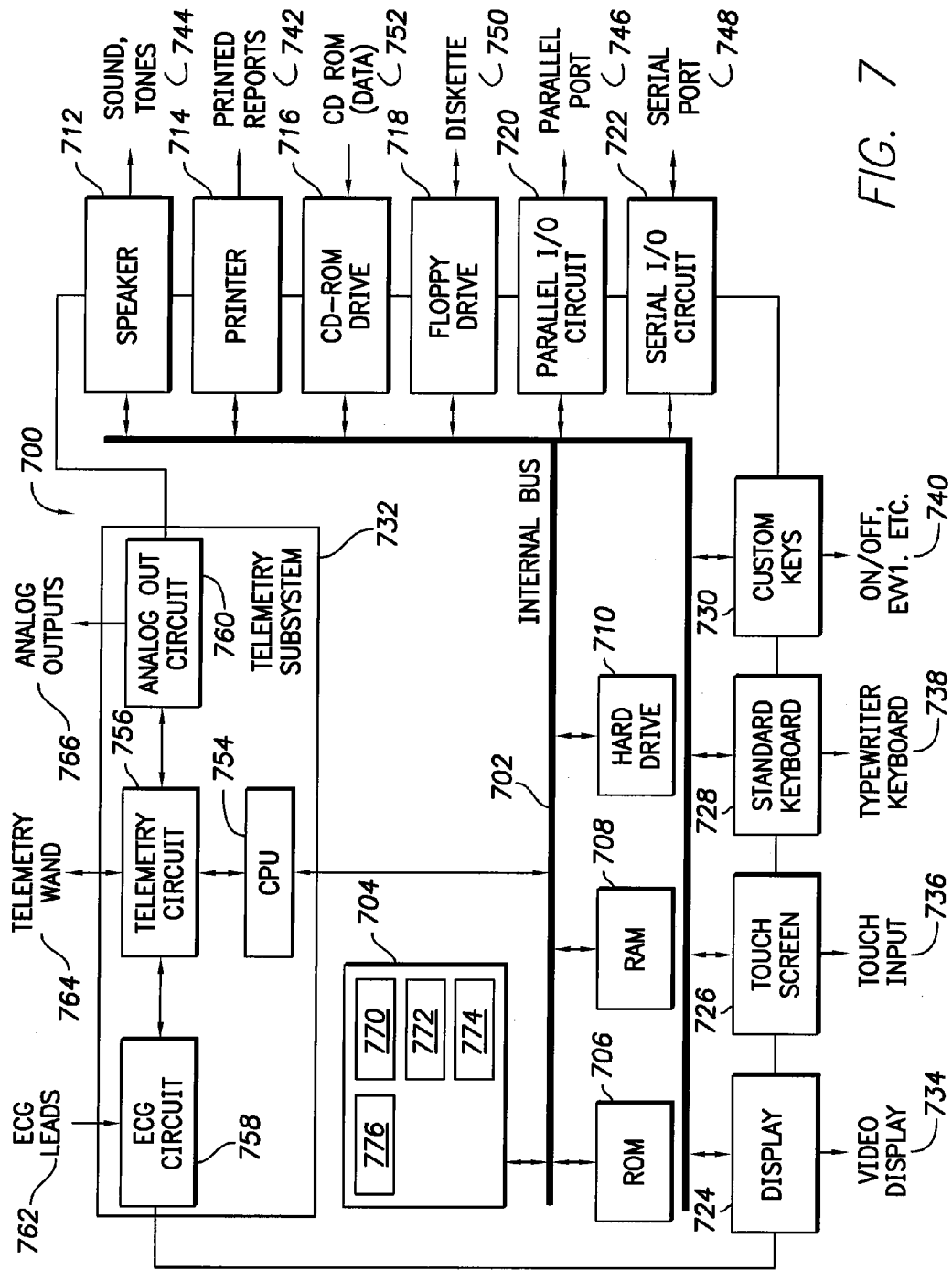
FIG. 7 illustrates a functional block diagram of an external device that may be implemented in accordance with an embodiment.

FIG. 7 illustrates a functional block diagram of the external device 700, such as a programmer that is operated by a physician, a health care worker, or a patient to interface with IMD 500 (shown in FIG. 5). The external device 700 may be utilized in a hospital setting, a physician's office, or even the patient's home to communicate with the IMD 500 to change a variety of operational parameters regarding the therapy provided by the IMD 500 as well as to select among physiological parameters to be monitored and recorded by the IMD 500. For example, the external device 700 may be used to program coronary episode related parameters, such as ECI values, ECI templates, ECI thresholds, HDP thresholds, and the like. Further, the external device 700 may be utilized to interrogate the IMD 500 to determine the condition of a patient, to adjust the physiological parameters monitored or to adapt the therapy to a more efficacious one in a non-invasive manner. Further, the external device 600 may represent an external PSA used during implant of an IMD. The external device 700, when used as a PSA during implant of an IMD, is in accordance with the intraoperative procedures described herein. The PSA would be connected to leads as described herein to delivery therapies. The external device 700 may include all of the connections, switch network, sensors, generators, arrhythmia detection, ECI measurement, HDP assessment and therapy delivery capabilities of an IMD such as in FIG. 6.

External device 700 includes an internal bus 702 that connects/interfaces with a processor module 704, ROM 706, RAM 708, a hard drive 710, a speaker 712, a printer 714, a CD-ROM drive 716, a floppy drive 718, a parallel I/O circuit 720, a serial I/O circuit 722, the display 724, a touch screen 726, a standard keyboard connection 728, custom keys 730, and a telemetry subsystem 732. The internal bus 702 is an address/data bus that transfers information (e.g., either memory data or a memory address from which data will be either stored or retrieved) between the various components described. The hard drive 710 may store operational programs as well as data, such as reference ST segments, ST thresholds, impedance thresholds, other thresholds, timing information and the like.

The CPU 704 typically includes a microprocessor, a microcontroller, or equivalent control circuitry, designed specifically to control interfacing with the external device 700 and with the IMD 500 (shown in FIG. 5). The CPU 704 may further include RAM or ROM memory, logic and timing circuitry, state machine circuitry, and I/O circuitry to interface with the IMD 100. Typically, the CPU 704 includes the ability to process or monitor input signals (e.g., data) as controlled by program code stored in memory (e.g., ROM 706).

The modules in the processor module 704 that monitor arrhythmias and HDP include an arrhythmia monitoring module 770, the impedance detection module 772, a HDP assessment module 774 and a therapy module 776. The arrhythmia monitoring module 770 determines segment variations such as ST segment variations and changes in the amplitude and rate of the R-wave. The impedance detection module 772 measures and/or calculates one or more of the first, second and third ECI impedance vectors Z1, Z2 and Z3. The HDP assessment module 774 monitors the HDP condition based on changes in the impedance vectors monitored by the impedance detection module 772. The therapy control module 776 assesses and determines what therapy to deliver. The therapy control module 776 declaring ICI based therapies, IEGM based therapies and ECI based therapies. The therapy control module 776 over-ruling and confirming ICI based therapy and non-therapy judgments utilizing ECI information.

For example, the HDP assessment module 674 may determine maximum impedance maxZ, impedance change per unit time ($\Delta Z/\Delta T$), change in hemodynamic performance, as well as any other parameters illustrated and discusses in connection with FIGS. 3 and 4. The HDP assessment module 674 may determine a difference between baseline and new impedance parameters and identify whether the difference exceeds threshold limits.

The display 724 (e.g., may be connected to a video display 734) and the touch screen 726 display text, alphanumeric information, data and graphic information via a series of menu choices to be selected by the user relating to the IMD 500, such as for example, status information, operating parameters, ECI parameters, HDP parameters, therapy parameters, patient status, access settings, software programming version, ST segment thresholds, impedance thresholds, HDP thresholds, other thresholds, and the like. The touch screen 726 accepts a user's touch input 736 when selections are made. The keyboard 728 (e.g., a typewriter keyboard 738) allows the user to enter data to the displayed fields, operational parameters, therapy parameters, as well as interface with the telemetry subsystem 732. Furthermore, custom keys 730 turn on/off 740 (e.g., EVVI) the external device 700. The printer 714 prints hard-copies of reports 742 for a physician/healthcare worker to review or to be placed in a patient file, and speaker 712 provides an audible warning (e.g., sounds and tones 744) to the user in the event a patient has any abnormal physiological condition occur while the external device 700 is being used. The parallel I/O circuit 720 interfaces with a parallel port 746. The serial I/O circuit 722 interfaces with a serial port 748. The floppy drive 718 accepts diskettes 750. The CD-ROM drive 716 accepts CD ROMs 752.

The telemetry subsystem 732 includes a central processing unit (CPU) 754 in electrical communication with a telemetry circuit 756, which communicates with both an ECG circuit 758 and an analog out circuit 760. The ECG circuit 758 is connected to ECG leads 762. The telemetry circuit 756 is connected to a telemetry wand 764. The analog out circuit 732 includes communication circuits, such as a transmitting antenna, modulation and demodulation stages (not shown), as well as transmitting and receiving stages (not shown) to communicate with analog outputs 766. The external device 700 may wirelessly communicate with the IMD 500 and utilize protocols, such as Bluetooth, GSM, infrared wireless LANs, HIPERLAN, 3G, satellite, as well as circuit and packet data protocols, and the like. A wireless RF link utilizes a carrier signal that is selected to be safe for physiologic transmission through a human being and is below the frequencies associated with wireless radio frequency transmission. Alternatively, a hard-wired connection may be used to connect the external device 700 to IMD 500 (e.g., an electrical cable having a USB connection).

Figure 8:
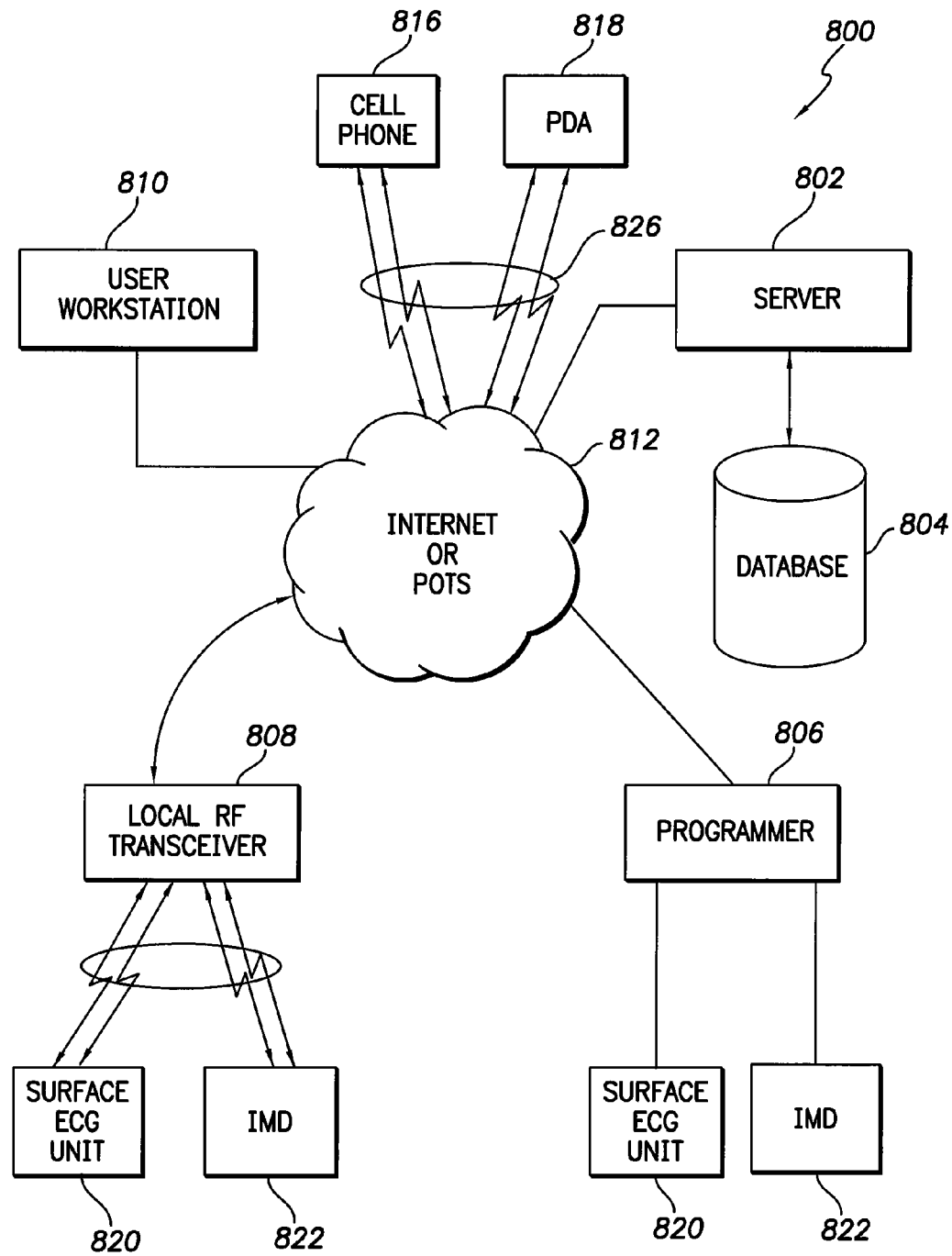
FIG. 8 illustrates a distributed processing system that may be implemented in accordance with one embodiment.

FIG. 8 illustrates a distributed processing system 800 in accordance with one embodiment. The distributed processing system 800 includes a server 802 that is connected to a database 804, a programmer 806 (e.g., similar to external device 700 described above and shown in FIG. 8), a local RF transceiver 808 and a user workstation 810 electrically connected to a communication system 812. The communication system 812 may be the internet, a voice over IP (VoIP) gateway, a local plain old telephone service (POTS) such as a public switched telephone network (PSTN), and the like. Alternatively, the communication system 812 may be a local area network (LAN), a campus area network (CAN), a metropolitan area network (MAN), or a wide area network (WAM).

The server 802 is a computer system that provides services to other computing systems (e.g., clients) over a computer network. The server 802 acts to control the transmission and reception of information (e.g., cardiac signals, processed cardiac signals, hemodynamic performance, ST segments, R-waves, thresholds, impedances, histograms, statistical analysis, trend lines, and the like). The server 802 interfaces with the communication system 812, such as the internet or a local POTS based telephone system, to transfer information between the programmer 806, the local RF transceiver 808, the user workstation 810 as well as a cell phone 816, and a personal data assistant (PDA) 818 to the database 804 for storage/retrieval of records of information. For instance, the server 802 may download or upload, via a wireless connection 826, to/from the cell phone 816 or the PDA 818 the results of processed cardiac signals, ST segment trends, impedance vectors, or a patient's physiological state (e.g., is the patient having or has had an ischemia) based on previously recorded cardiac information. The server 802 may upload raw cardiac signals (e.g., unprocessed cardiac data) from a surface ECG unit 820 or an IMD 822 via the local RF transceiver 808 or the programmer 806.

The database 804 stores information such as raw cardiac data, processed cardiac signals, HDP, ECI values, ECI waveforms, statistical calculations (e.g., averages, modes, standard deviations), histograms, cardiac trends (e.g., STS trends), and the like. The information is downloaded into the database 804 via the server 802 or, alternatively, the information is uploaded to the server from the database 804.

The programmer 806 is similar to the external device 700 shown in FIG. 7 and described above, and may reside in a patient's home, a hospital, or a physician's office. Programmer 806 interfaces with the surface ECG unit 820 and the IMD 822 (e.g., similar to the IMD 500 described above and shown in FIG. 5). The programmer 806 may wirelessly communicate with the IMD 822 and utilize protocols, such as Bluetooth, GSM, infrared wireless LANs, HIPERLAN, 3G, satellite, as well as circuit and packet data protocols, and the like. Alternatively, a hard-wired connection may be used to connect the programmer 806 to IMD 500 (e.g., an electrical cable having a USB connection). The programmer 806 is able to acquire cardiac signals from the surface of a person (e.g., ECGs), or the programmer is able to acquire intra-cardiac electrogram (e.g., IEGM) signals from the IMD 822.

The local RF transceiver 808 interfaces with the communication system 812, to upload cardiac data, ECI measurements, HDP acquired from the surface ECG unit 820 or the IMD 822 to the server 802. In one embodiment, the surface ECG unit 820 and the IMD 822 have a bi-directional connection with the local RF transceiver via a wireless connection.

The user workstation 810 may interface with the communication system 812 to download information via the server 802 from the database 804. Alternatively, the user workstation 810 may download raw data from the surface ECG unit 820 or IMD 822 via either the programmer 806 or the local RF transceiver 808. Once the user workstation 810 has downloaded the cardiac information (e.g., raw cardiac signals, ST segments, HDP, ECI measurements, impedance vectors, and the like), the user workstation 810 may process the cardiac signals, HDP, ECI measurements, create histograms, calculate statistical parameters, or determine trends and determine if the patient is suffering from insufficient HDP or another physiological condition. Once the user workstation 810 has finished performing its calculations, the user workstation 810 may either download the results to the cell phone 816, the PDA 818, the local RF transceiver 808, the programmer 806, or to the server 802 to be stored on the database 804.

In accordance with an embodiment, a method and system are provided that afford long term remote patient monitoring of AF using cardiogenic impedance. The impedance measurements are used to characterize HDP, such as cardiac output or another HDP related indicator. The impedance measurements and/or HDP information is conveyed over a home based monitoring network to provide remote monitoring of AF episodes and AF burden utilizing cardiogenic impedance based information.

Figure 11:
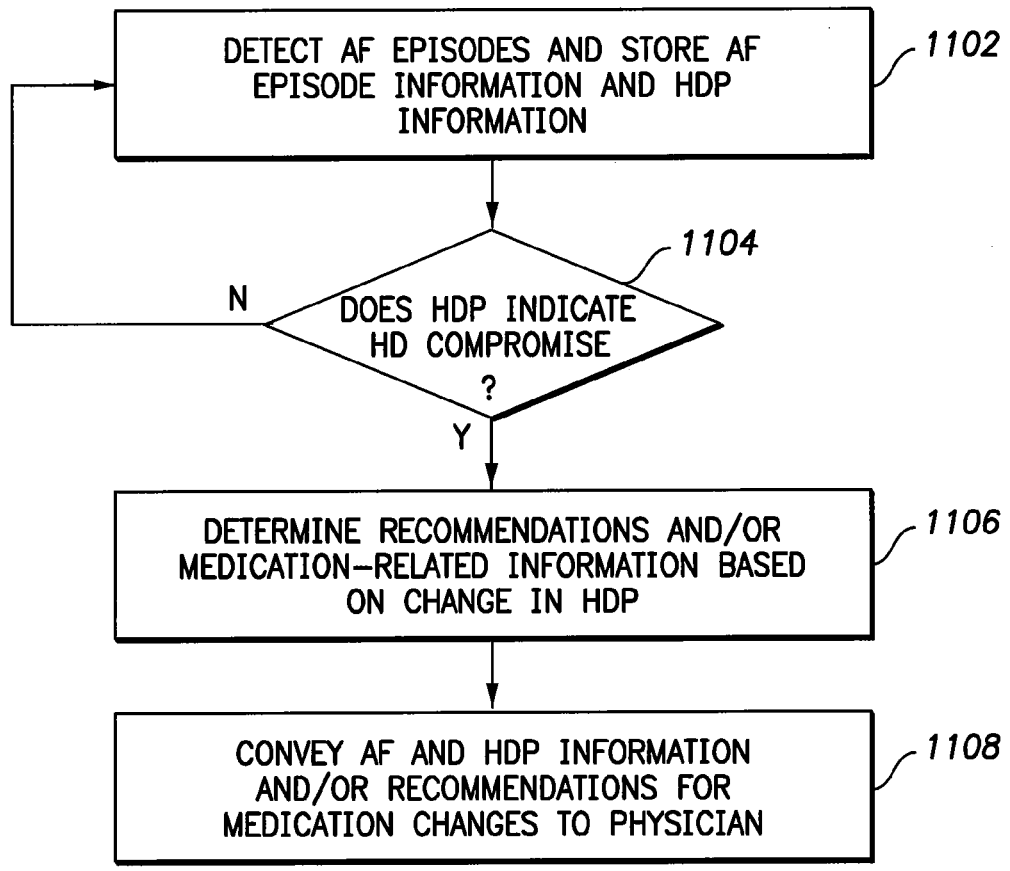
FIG. 11 illustrates a flow chart for a method implemented in accordance with an embodiment.

FIG. 11 illustrates a flow chart for a method implemented in accordance with an embodiment. At 1102, the IMD detects AF episodes over time (e.g., over day, week, month, year) and stores AF episode information. The AF episode information may include the IEGM signal during the episode, during onset of the episode and during completion of the episode. The AF episode information may include number of AF episodes, the duration of the AF episodes, the AF burden (e.g., percentage of time in AF out of a predetermined period of time). At 1102, the IMD also saves, for each AF episode, hemodynamic performance (HDP) information. The HDP information may include hemodynamic performance among other things, as well as contractility, strength of contractions, consistency of contractions and the like.

At 1104, it is determined whether the HDP has deteriorated by an amount sufficient to indicate HD compromise. If not, flow returns to 1102. If yes, flow moves to 1106. HD compromise may be determined when the HDP level falls below a baseline HDP level by a predetermined amount (e.g., percentage or programmed amount). For example, an HDP baseline may be set under physician control or obtained automatically periodically during normal sinus rhythm. Thereafter, each time an AF episode is detected, the HDP is determined and compared to the baseline. When the change in HDP exceeds a threshold, the IMD may output an HDP compromise indication. The compromise indication may be conveyed to a physician. For example the IMD may transmit a series of HDP valves to a physician. The physician may use the HDP valves to determine a change in the prescription medicine (e.g., increase, add, reduce or remove dosage of Digitalis or a calcium channel blocker).

At 1106, the method may provide a physician with recommendations or medicine related information. For example, it may provide a recommendation to change a type or dosage of medication. For example, it may suggest adding or increasing dosage of a calcium channel blocker to reduce conductivity of the AV node.

HDP information and AF episode information may be transmitted from the IMD periodically (e.g., daily) or only when certain criteria are satisfied (e.g., scheduled follow-ups). The HDP and AF information may then be conveyed over a network (e.g., the internet) to a physician, a hospital, a database or central network server. With reference to FIG. 8, the IMD 822 may communicate with a home base RF-wireless transmitter 808 (e.g., the Merlin™@home transmitter). The transmitter 808 downloads HDP and AF information from the IMD and then transmits the HDP and AF information to a network, internet, telephone, cellular wireless link and the like. The HDP and AF information may be sent to a secure internet based data management system 802, 804 (e.g., the Merlin.net PCN system). The system 802, 804, stores the HDP and AF information for review and use by physicians. The system 802, 804 can perform daily checks to monitor for alerts about performance and heart rhythms. The system 802, 804 can be programmed to alert physicians directly. Optionally, the IMD 822 may convey the HDP and AF information directly to the programmer 806. The programmer 806 may display the HDP and AF information to a physician, and/or analyze the HDP and AF information to provide recommendations to physicians, such as at 1106.

At 1108, the HDP and AF information are conveyed to a physician's workstation 810, cell phone 816, PDA 818 and the like. At 1108, the method may also convey recommendations for changes in medication and/or medication related information to the physician's workstation 810, cell phone 816 or PDA 818. The analysis to reach a recommendation (at 1106) may be performed in whole or in part at one or more of the IMD 822, programmer 806, server 802, workstation 810, cell phone 816, PDA 818 and the like.

Figure 12:
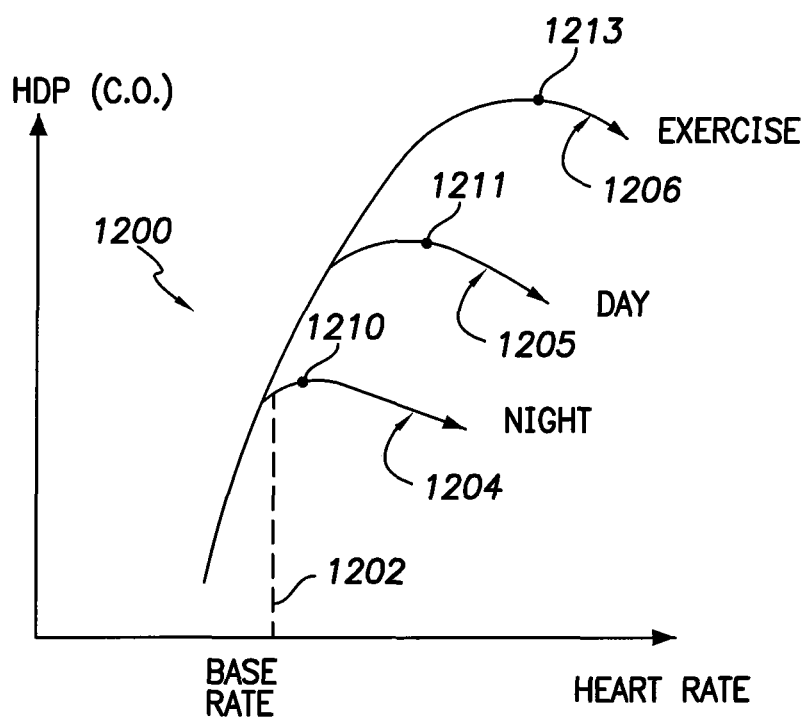
FIG. 12 illustrates a graph plotting an exemplary relation between hemodynamic performance and heart rate along the horizontal axis.

FIG. 12 illustrates a graph plotting an exemplary relation between hemodynamic performance (denoted HDP on the vertical axis) and heart rate along the horizontal axis. The graph 1200 includes a point 1202 that corresponds to a base pacing rate of a pacemaker. The graph 1200 illustrates that the relation between the heart rate and the HDP may differ depending upon the reason for the elevated heart rate. Curves 1204-1206 plot different relations between heart rate and HDP based on the reason for the reason for the elevation in heart rate. In the example of FIG. 12, curve 1204 represents physiologic behavior that may occur when a patient is lying down and sleeping, curve 1205 represents physiologic behavior that may occur when a patient is standing up and is awake, and curve 1206 represents physiologic behavior that may occur when a patient is exercising.

Heart rate increase due to exercise is generally a normal and healthy physiologic behavior. The relation between heart rate and HDP follows curve 1206, in which the HDP continues to improve to a relatively high level that is associated with a relatively high heart rate. A maximum HDP occurs at 1213 which is relatively distal to the base pacing rate 1202. Heart rate increase not due to exercise, and while asleep is generally abnormal and un-healthy physiologic behavior. The relation between heart rate and HDP follows curve 1204, in which the HDP does not improve with higher heart rate. A maximum HDP occurs at 1210 which is relatively close to the base pacing rate 1202. Heart rate increase not due to exercise and while awake, falls between curves 1204 and 1206. The relation between heart rate and HDP follows curve 1205, in which the HDP improves some with higher heart rate. A maximum HDP occurs at 1211 which is at an intermediate rate above the base pacing rate 1202.

In accordance with an embodiment, a method and system are provided to adjust a pacing rate of an IMD based on the ECI measurements to obtain a HDP-related pacing rate that affords a predetermined hemodynamic performance. Optionally, the IMD may receive an output from a motion sensor representing at least one of 3D posture movement and a level of exercise. The IMD adjusts a pacing rate of the IMD based on the ECI measurements and the output from the motion sensor.

During atrial fibrillation, the ventricles respond sporadically. When the ventricles are paced, the pacing stimulus places the AV node in a refractory state. The heart will exhibit different hemodynamic performance based on the temporal relation between onset of an AF episode and the refractory state of the AV node. By varying the pacing rate, the IMD changes the time period when the AV node is in the refractory state. Thus, by varying the pacing rate, the IMD is also able to impact the hemodynamic performance of the heart. In accordance with embodiments herein, a method and system are provided in which the pacing rate is adjusted in order to improve a level of hemodynamic performance.

Figure 13:
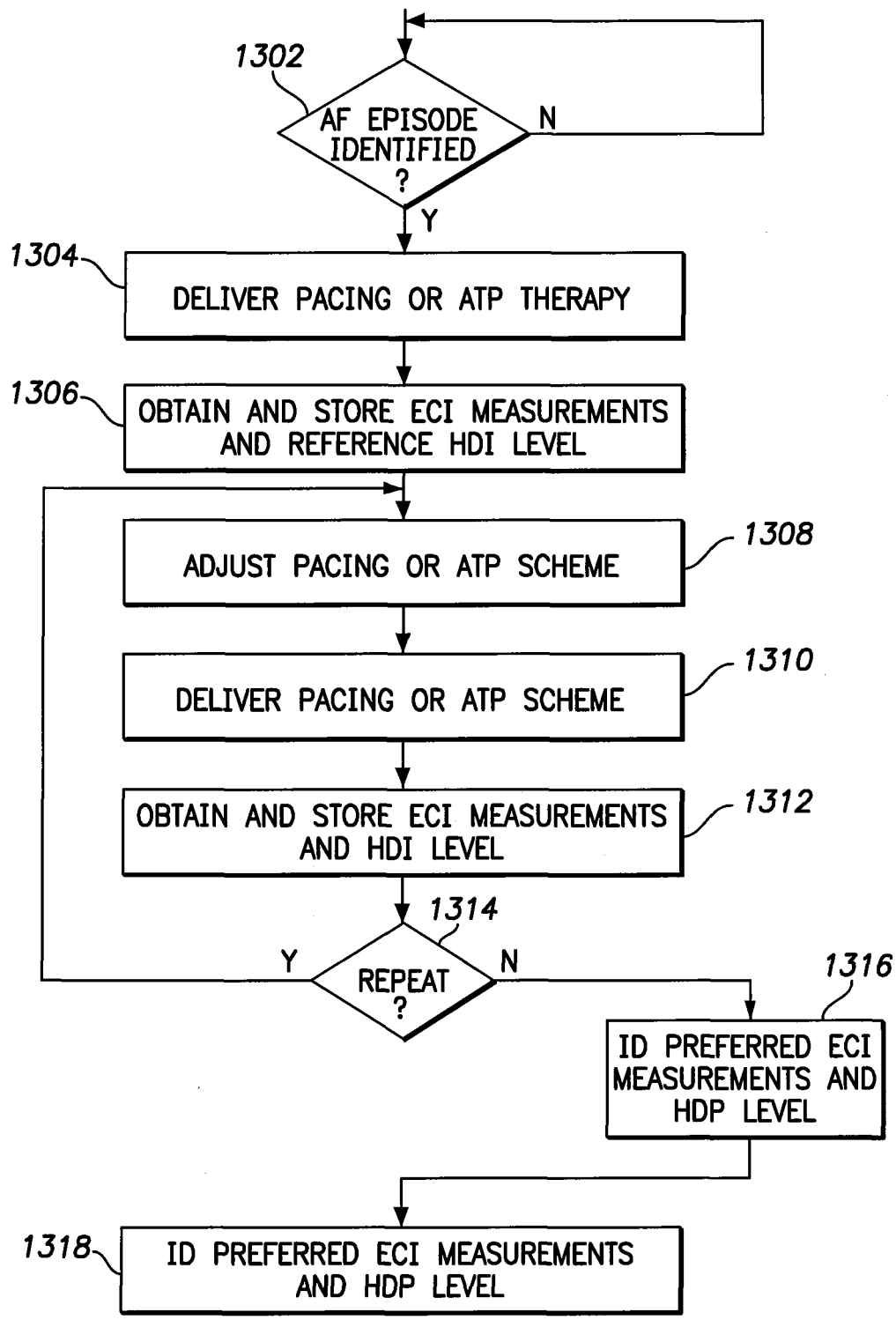
FIG. 13 illustrates a process for a method for adjusting the pacing rate in order to improve a level of hemodynamic performance.

FIG. 13 illustrates a process for a method for adjusting the pacing rate in order to improve a level of hemodynamic performance. Beginning at 1302, an AF episode is identified. At 1304, the IMD delivers one or more pacing pulses or antitachy pacing (ATP) pulses in accordance with a base or preprogrammed rate. At 1306, ECI measurements are obtained and a reference HDP level is calculated. At 1308, the pacing scheme or ATP scheme is adjusted. For example, the adjustment may represent a change in the pacing rate, a change in the pacing lead configuration, a change in the pacing polarity and the like. Optionally, the adjustment may be to change a number of pulses in an ATP scheme, the delay between ATP pulses, the locations at which the ATP pulses are delivered, the ATP pulse polarity and the like. Once the pacing or ATP scheme has been adjusted, at 1310, the IMD delivers one or more pacing pulses or antitachy pacing (ATP) pulses in accordance with the current (adjusted) scheme. At 1312, ECI measurements are obtained and a current HDP level is calculated. At 1314, it is determined whether the operations at 1308-1312 should be repeated. The operations at 1308-1312 are repeated a predetermined number of times in order to obtain a desired number of ECI measurements and HDP levels for different pacing or ATP schemes.

Next, at 1316 the stored ECI measurements and/or HDP levels are analyzed to identify a preferred ECI measurement and/or HDP level. For example, the preferred ECI measurement and/or HDP level may represent a lowest ECI measurement or highest HDP level. At 1318, the IMD is then set to utilize the pacing or ATP scheme that corresponded with the preferred ECI measurement and/or HDP level.

In accordance with an embodiment, a medical system is provided that comprises an implantable medical device (IMD) coupled to a lead assembly configured to establish an extra-cardiac impedance (ECI) vector that extends through at least a portion of the greater vessels. The IMD includes a processor module to obtain ECI measurements along the ECI vector. The processor module obtains hemodynamic performance (HDP) information based on the ECI measurements. The processor module identifies atrial fibrillation (AF) episodes and collects AF information. The IMD includes memory to store at least one of AF information and HDP information. An external device is configured to communicate with the IMD. The external device includes a receiver to receive the at least one of AF information or HDP information from the IMD. The external device conveys the at least one of AF information and HDP information to a patient care network facility to afford remote monitoring of AF episodes in connection with ECI measurements. The system further includes a database located at the patient care network facility to store the at least one of AF information and HDP information in connection with long term patient monitoring.

The system further comprises a physician operated device configured to receive the at least one of AF information and HDP information. The physician operated device represents at least one of a workstation, laptop, phone and personal digital assistant. The external device may be located in a home of a patient to afford remote home based monitoring of AF episodes. The external device may be a programmer configured to be operated by a physician. The system further comprises an analysis module to analyze the HDP information and obtain medication related information based on the HDP information. The analysis module is located at one or more of the IMD, the external device and the patient care network facility. The medication related information may include recommendations regarding at least one of type and dosage of medication. The IMD may include an arrhythmia monitoring module configured to analyze intra-cardiac electrogram (IEGM) signals in connection with identification of the AF episodes.

In accordance with an embodiment, a method is provided remote long term monitoring of atrial fibrillation (AF) episodes. The method includes obtaining extra-cardiac impedance (ECI) measurements along an ECI vector that extends through at least a portion of the greater vessels and determining hemodynamic performance (HDP) information based on the ECI measurements. The method further includes identifying atrial fibrillation (AF) episodes and collecting AF information related thereto and transmitting the at least one of AF information and HDP information from the IMD to an external device. The method further includes conveying the at least one of AF information and HDP information from the external device to a patient care network facility to afford remote monitoring of AF episodes in connection with ECI measurements.

The method further comprises storing the at least one of AF information and HDP information in a database located at the patient care network facility in connection with long term patient monitoring. A physician operated device is configured to receive the at least one of AF information or HDP information. The method further comprises analyzing the HDP information and obtaining medication related information based on the HDP information. The medication related information includes recommendations regarding at least one of type and dosage of medication. It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method for assessing hemodynamic stability, comprising:
providing a lead assembly including at least one intra-cardiac (IC) electrode, an extra-cardiac (EC) electrode and a subcutaneous remote-cardiac (RC) electrode, the IC electrode configured to be located within the heart, the EC electrode configured to be positioned proximate to at least one of a superior vena cava (SVC) and a left ventricle (LV) of a heart, the RC electrode configured to be located remote from the heart;
analyzing intra-cardiac electrogram signals from the at least IC electrode to identify a potential atrial arrhythmia;
measuring extra-cardiac impedance along an extra-cardiac impedance (ECI) vector between the EC and RC electrodes to obtain ECI measurements, the ECI vector extending through at least a portion of the greater vessels, the ECI measurements having a respiratory component and a cardiac component;
filtering the ECI measurements to remove the respiratory component;
determining a EC hemodynamic performance based on the filtered ECI measurements; and
declaring the potential atrial arrhythmia to be an atrial arrhythmia based on the EC hemodynamic performance determined from the ECI measurements.

2. The method of claim 1, wherein the ECI vector extends through at least a portion of the greater vessels and substantially bypasses an intra-cardiac blood pool.

3. The method of claim 1, further comprising deriving a current ECI waveform from current ECI measurements, and comparing the current ECI waveform with a prior ECI waveform derived from prior ECI measurements, wherein the current and baseline ECI measurements represent surrogates for aortic blood flow.

4. The method of claim 1, further comprising deriving ECI waveforms from the ECI measurements and identifying changes in a current ECI waveform derived from current ECI measurements, wherein the ECI measurements represent a surrogate for aortic blood flow.

5. The method of claim 1, further comprising obtaining ventricular IEGM (V-IEGM) signals from the intra-cardiac electrogram signals from the at least one IC electrode and measuring ST elevation from the V-IEGM signals to assess potential acute ischemia or chronic myocardial infarction.

6. The method of claim 1, further comprising deriving ECI waveforms from the ECI measurements and analyzing a peak-to-peak amplitude in the ECI waveforms derived from the ECI measurements to assess hemodynamic stability and to determine whether sufficient EC hemodynamic performance exists.

7. The method of claim 1, further comprising obtaining baseline ECI measurements; analyzing current ECI measurements relative to the baseline ECI measurements to obtain surrogates for current and baseline beat-by-beat stroke volumes; and determining whether sufficient EC hemodynamic performance exists based on a comparison of the surrogates for the current and baseline beat-by-beat stroke volumes.

8. The method of claim 1, further comprising adjusting a pacing rate of the IMD based on the ECI measurements to obtain a HDP-related pacing rate that affords a predetermined EC hemodynamic performance.

9. The method of claim 1, further comprising receiving an output from a motion sensor representing at least one of 3D posture movement and a level of exercise; and adjusting a pacing rate of the IMD based on the ECI measurements and the output from the motion sensor.

10. A medical device, comprising:
a lead assembly including at least one intra-cardiac (IC) electrode, an extra-cardiac (EC) electrode and a subcutaneous remote-cardiac (RC) electrode, the IC electrode configured to be located within the heart, the EC electrode configured to be positioned proximate to at least one of a superior vena cava (SVC) and a left ventricle (LV) of a heart, the RC electrode configured to be located remote from the heart;
arrhythmia monitoring module configured to analyze intra-cardiac electrogram (IEGM) signals from the at least one IC electrode to identify a potential atrial arrhythmia;
extra-cardiac impedance (ECI) module configured to measure extra-cardiac impedance along an ECI vector between the EC and RC electrodes to obtain ECI measurements, the ECI measurements having a respiratory component and a cardiac component; and hemodynamic performance (HDP) assessment module configured to filter the ECI measurements to remove the respiratory component and to determine EC hemodynamic performance based on the filtered ECI measurements, the arrhythmia monitoring module configured to declare the potential atrial arrhythmia to be an atrial arrhythmia based on the EC hemodynamic performance determined from the ECI measurements.

11. The device of claim 10, wherein the ECI vector extends through at least a portion of the greater vessels and substantially bypasses an intra-cardiac blood pool.

12. The device of claim 10, wherein the HDP assessment module derives a current ECI waveform from current ECI measurements and compares the current ECI waveform with a baseline ECI waveform that is derived from baseline ECI measurements, wherein the current and baseline ECI measurements represent surrogates for aortic blood flow.

13. The device of claim 10, wherein the HDP assessment module identifies changes in a current ECI waveform that is derived from current ECI measurements, wherein the current ECI measurements represent a surrogate for aortic blood flow.

14. The device of claim 10, wherein the HDP assessment module configured to determine, as the EC hemodynamic performance, one or more of cardiac output, stroke volume, systolic blood pressure or diastolic blood pressure, based on the ECI measurements associated with blood flow through at least a portion of the greater vessels.

15. The device of claim 10, wherein the ECI vector substantially bypasses an intra-cardiac blood pool and passes through at least a portion of at least one of pulmonary arteries, pulmonary veins, brachiocephalic arteries and brachiocephalic veins, left carotid artery and left subclavian artery.

16. The device of claim 10, further comprising a motion sensor, wherein the arrhythmia monitoring module is configured to analyze 3D posture movement based on an output from the motion sensor, the arrhythmia monitoring module configured to declare the potential atrial arrhythmia to be an atrial arrhythmia based on the 3D posture movement.

17. The device of claim 10, further comprising a breathing rate sensor, wherein the arrhythmia monitoring module is configured to analyze a breathing rate based on an output from the breathing rate sensor.

18. The device of claim 10, wherein the HDP assessment module is configured to analyze parameters associated with the ECI measurements relative to ECI thresholds to determine whether sufficient EC hemodynamic performance exists.

19. The device of claim 10, further comprising memory configured to store baseline ECI values associated with baseline ECI measurement obtained when normal EC hemodynamic performance is present, the HDP assessment module utilizing the baseline ECI values to analyze current ECI measurements to determine whether sufficient EC hemodynamic performance exists.

20. The device of claim 10, further comprising a therapy control module configured to determine whether to apply a corrective therapy based on the ECI measurements and the IEGM signals.

21. The device of claim 10, wherein the HDP assessment module determines whether the EC hemodynamic performance is hemodynamically stable or unstable based on the ECI measurement, the device further comprising a therapy control module that suspends an IEGM based therapy when the ECI measurements indicate that the EC hemodynamic performance is hemodynamically stable.

\* \* \* \* \*